(12) United States Patent
Herrmann et al.

(10) Patent No.: US 10,105,311 B2
(45) Date of Patent: Oct. 23, 2018

(54) MICROCAPSULES CONTAINING A GAS-GENERATING PHOTOLABILE POLYMER AND USES THEREOF

(71) Applicant: Firmenich SA, Geneva (CH)

(72) Inventors: Andreas Herrmann, Geneva (CH); Damien Berthier, Geneva (CH); Serge Lamboley, Geneva (CH); Nicolas Paret, Geneva (CH)

(73) Assignee: Firmenich SA, Geneva (CH)

( * ) Notice: Subject to any disclaimer, the term of this patent is extended or adjusted under 35 U.S.C. 154(b) by 1 day.

(21) Appl. No.: 15/528,657

(22) PCT Filed: Nov. 23, 2015

(86) PCT No.: PCT/EP2015/077390
§ 371 (c)(1),
(2) Date: May 22, 2017

(87) PCT Pub. No.: WO2016/083321
PCT Pub. Date: Jun. 2, 2016

(65) Prior Publication Data
US 2017/0266103 A1 Sep. 21, 2017

(30) Foreign Application Priority Data
Nov. 24, 2014 (EP) ..................................... 14194578

(51) Int. Cl.
| | | |
|---|---|---|
| A61K 8/11 | (2006.01) | |
| B01J 13/02 | (2006.01) | |
| A61K 8/81 | (2006.01) | |
| A61K 8/91 | (2006.01) | |
| C11D 3/50 | (2006.01) | |
| A61Q 13/00 | (2006.01) | |
| A61K 8/37 | (2006.01) | |
| A61K 8/85 | (2006.01) | |

(52) U.S. Cl.
CPC .................. *A61K 8/91* (2013.01); *A61K 8/11* (2013.01); *A61K 8/37* (2013.01); *A61K 8/8105* (2013.01); *A61K 8/8158* (2013.01); *A61K 8/85* (2013.01); *A61Q 13/00* (2013.01); *B01J 13/02* (2013.01); *C11D 3/505* (2013.01); *C11D 3/507* (2013.01); *A61K 2800/412* (2013.01)

(58) Field of Classification Search
CPC .......... A61K 8/11; A61K 8/37; A61K 8/8105; A61K 8/8158; A61K 8/85; A61K 8/91; A61K 2800/412; A61Q 13/00; B01J 13/02; C11D 3/505; C11D 3/507
See application file for complete search history.

(56) References Cited

U.S. PATENT DOCUMENTS

| | | | |
|---|---|---|---|
| 3,301,439 A | 1/1967 | Kosar et al. | |
| 4,396,670 A | 8/1983 | Sinclair et al. | |
| 6,133,228 A * | 10/2000 | Pika ......................... | A61K 8/37 512/21 |
| 6,369,026 B1 * | 4/2002 | Pika ......................... | A61K 8/37 512/21 |
| 9,738,859 B2 * | 8/2017 | Herrmann .............. | A61K 8/365 |
| 2007/0202063 A1 | 8/2007 | Dihora et al. | |

FOREIGN PATENT DOCUMENTS

| | | |
|---|---|---|
| EP | 1741775 A1 | 1/2007 |
| GB | 2432843 A | 6/2007 |
| GB | 2432850 A | 6/2007 |
| GB | 2432851 A | 6/2007 |
| GB | 2432852 A | 6/2007 |
| WO | WO1999060990 A2 | 12/1999 |
| WO | WO2001041915 A1 | 6/2001 |
| WO | WO2005054422 A1 | 6/2005 |
| WO | WO2007062733 A1 | 6/2007 |
| WO | WO2007062833 A1 | 6/2007 |
| WO | WO2008016684 A1 | 2/2008 |
| WO | WO2011161618 A1 | 12/2011 |
| WO | WO2013079435 A1 | 6/2013 |
| WO | WO2014187833 A1 | 11/2014 |

OTHER PUBLICATIONS

International Search Report and Written Opinion, application PCT/EP2015/077390, dated Feb. 10, 2016.
Bonatz et al., Acta Polymerica 40 (1989), p. 683-690.
Bône et al., Chimia, 2011, vol. 65, p. 177-181.
Braslavsky, IUPAC, Pure and Applied Chemistry, 2007, vol. 79, p. 293-465.
Dietrich et al., Acta Polymerica, 1989, vol. 40, n° 4, p. 243.
Dietrich et al., Acta Polymerica, 1989, vol. 40, n° 5, p. 325.
Dietrich et al. Acta Polymerica, 1990, vol. 41, p. 91-95.
Lee et al., J. Microencapsulation, 2002, vol. 19 No. 5, p. 559-569.

* cited by examiner

*Primary Examiner* — Irina S Zemel
(74) *Attorney, Agent, or Firm* — Winston & Strawn LLP

(57) ABSTRACT

The present invention relates to water-dispersable microcapsules comprising an oil phase, e.g. a perfume, containing a photolabile polymer comprising α-ketoacid or α-ketoester group capable of generating a gas upon exposure to light. The gas is able to cause an extension or the breaking of the microcapsule allowing the release of the oil phase and thus increasing the long-lastingness of the odor perception. The present invention concerns also the use of said microcapsules in perfumery as well as perfuming compositions or perfumed articles comprising the invention's microcapsules to provide a prolonged release of fragrant molecules.

18 Claims, 1 Drawing Sheet

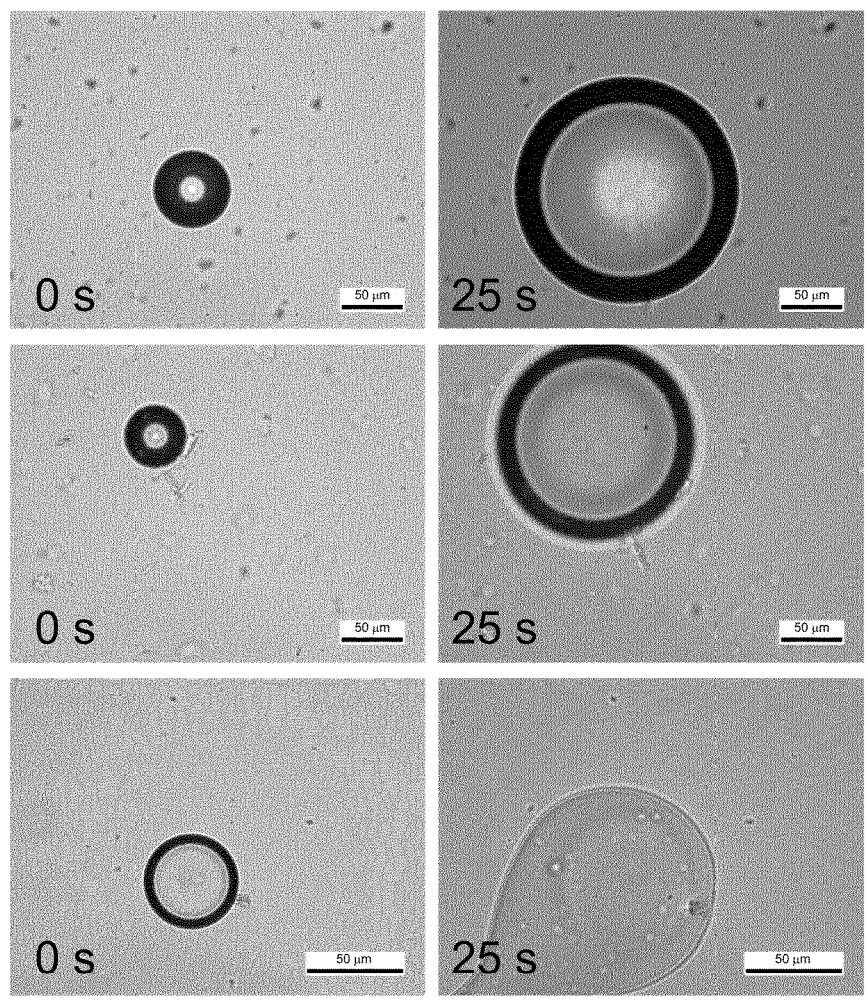

MICROCAPSULES CONTAINING A GAS-GENERATING PHOTOLABILE POLYMER AND USES THEREOF

This application is a 371 filing of International Patent Application PCT/EP2015/077390 filed 23 Nov. 2015, which claims the benefit of European patent application no 14194578.2 filed Nov. 24, 2014, the entire contents of which are hereby incorporated by reference in their entirety.

TECHNICAL FIELD

The present invention relates to water-dispersible microcapsules capable of increasing the long-lastingness of active compounds and releasing those compounds upon exposure to light. The invention concerns the encapsulation of a photolabile polymer comprising a ketoacid or ketoester group capable of releasing a gas, so as to expand or break the capsule wall, and thus to trigger the release of an oil phase containing at least one active compound capable of bringing a benefit or effect into the surrounding environment. The invention further concerns the use of the resulting microcapsules in consumer products.

PRIOR ART

One of the problems faced by the perfume industry lies in the relatively rapid loss of the olfactive benefit provided by odoriferous compounds as a result of their volatility, particularly that of "top-notes". Also, some fragrance ingredients can be unstable in applications of functional perfumery and get lost due to degradation or to rapid evaporation. These problems are often tackled through the use of delivery systems, e.g. capsules containing a perfume, to release the fragrance in a controlled manner.

Encapsulation of a fragrance can at least partially solve the evaporation problem, but many types of microcapsules are known to lose parts of the fragrance during storage, via diffusion through their shells or walls or as a result of the nature of the consumer product into which they are incorporated and which contains surface active ingredients capable of causing leakage of the perfume.

To perceive the encapsulated perfume, one either needs to mechanically break the microcapsules or to generate a spontaneous leakage of the perfume out of the capsules at the desired time. In the first case, the olfactive experience is limited to scratching episodes, while in the second case, one usually encounters problems of performance due to issues related to the limited shelf-life of the consumer product containing the microcapsules.

In WO2013/079435 and WO2014/187833 report the encapsulation of a photolaphile compound comprising a 2-oxoacetate group which decompose upon exposure to light allowing to create systems addressing the above-cited problems. However the degradation of these photolabile compounds could in the same time liberate small volatiles molecules having a bad olfactive impact.

So there is still a need to improve such a system. According to the invention, the fragrance is encapsulated within a solid shell or membrane or yet is part of a matrix system together with a polymer which is able to cause an extension or the breaking of the microcapsule and thus triggering the olfactive experience without requiring a scratching episode or relying on a leakage phenomenon which is difficult to control.

The solution proposed by the invention applies to many other benefit agents.

We have now been able to establish that the encapsulation of a photolabile polymer able to generate a gas inside microcapsules resulted in the desired effect, i.e. the spontaneous extension or breaking of the microcapsule upon exposure to light while avoiding release of undesired volatile side-products that could interfere with the benefit agent to be released during light-induced generation of a gas from a polymer. Furthermore, this effect is surprising because one might have expected that the unfavorable oil solubility of the polymer would have reduced the amount of photolabile polymer in the core of the capsule, thus limiting the generation of a gas inside the core leading to the extension or the breaking of the microcapsule.

BRIEF DESCRIPTION OF THE DRAWINGS

FIG. 1: Optical microscope images of solutions of photolabile polymers comprising an α-ketoester according to the invention in different fragrance raw materials (50% by weight) before (0 s) and after exposure to UVA light (25 s); top: Polymer 4 of Example 1 in acetophenone, middle: Polymer 7 of Example 1 in benzyl benzoate, bottom: Polymer 8 of Example 1 in acetophenone.

DESCRIPTION OF THE INVENTION

One object of the present invention is a microcapsule comprising:
A) a core comprising, or consisting of:
   an oil phase;
   at least one photolabile linear or graft polymer comprising an α-ketoacid or α-ketoester group capable of generating, upon exposure to light at a wavelength comprised between 450 and 320 nm a gas selected among the group consisting of CO and $CO_2$ and comprising at least one unit of formula

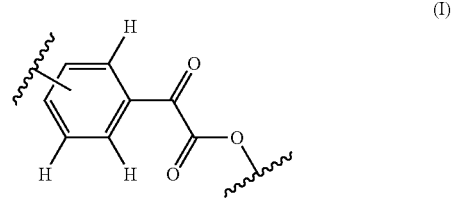

(I)

wherein said unit of formula (I) comprises a benzenediyl functional group substituted in meta or para position and is part of:
a) a backbone of a linear polymer of formula

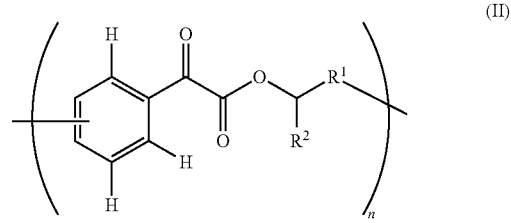

(II)

wherein n represents an integer varying between 2 and 1000, $R^1$ represents a $C_{1-8}$ hydrocarbon group and $R^2$ represents a hydrogen atom or a methyl group; or b) a side chain of a graft polymer of formula

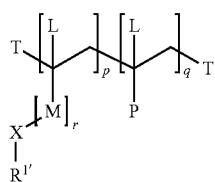
(III)

wherein
L is a hydrogen atom or a methyl group;
M represents a $C_{1-8}$ aliphatic hydrocarbon group optionally comprising one or two oxygen atoms and/or one nitrogen atom;
P represents, independently from each other, a $OR^3$ group; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a $CONLR^3$ group, a 2-oxopyrrolidin-1-yl group or a 2-oxoazepan-1-yl group, wherein $R^3$ represents a hydrogen atom, a $C_{1-18}$ alkyl group, a $(CH_2CH_2O)_mL$ group, a $(CHCH_3CH_2O)_mL$ group wherein m is an integer varying between 1 and 10 or a $CH_2(CH_2)_{2-3}OH$ group;
X represents the unit of formula (I) provided that the oxygen atom of the carboxyl functional group of the unit (I) is linked to a hydrogen atom or to a primary or secondary carbon atom;
$R^{1'}$ represents a hydrogen atom, a $C_{1-22}$ hydrocarbon group optionally comprising one to three oxygen atoms and/or one to two nitrogen atoms and/or one sulfur atom, or, if $R^{1'}$ is linked to the oxygen atom of the carboxyl functional group of the unit (I), an alkaline metal ion;
p is an integer varying between 5 and 1000;
q is an integer varying between 0 and 500;
r is an integer varying between 0 and 1; and
T is a polymer terminating group;
optionally comprising at least one photo-catalyst; and
B) a shell surrounding said core formed by interfacial polymerization, by a phase separation process induced by polymerization or by coacervation.

According to a particular embodiment of this invention, said microcapsule comprises:
A) a core comprising, or consisting of:
an oil phase;
at least one photolabile linear or graft polymer comprising an α-ketoacid or α-ketoester group capable of generating, upon exposure to light at a wavelength comprised between 450 and 320 nm a gas selected among the group consisting of CO and $CO_2$ and comprising at least one unit of formula

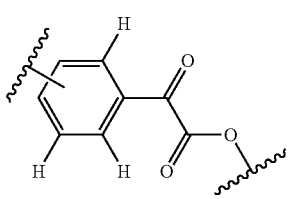
(I)

wherein said unit of formula (I) comprises a benzenediyl functional group substituted in meta or para position and is part of a side chain of graft polymer having a formula

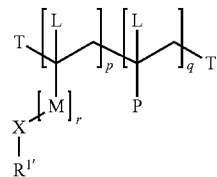
(III)

wherein
L is a hydrogen atom or a methyl group;
M represents a $C_{1-8}$ aliphatic hydrocarbon group optionally comprising one or two oxygen atoms and/or one nitrogen atom;
P represents, independently from each other, a $OR^3$ group; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a $CONLR^3$ group, a 2-oxopyrrolidin-1-yl group or a 2-oxoazepan-1-yl group, wherein $R^3$ represents a hydrogen atom, a $C_{1-18}$ alkyl group, a $(CH_2CH_2O)_mL$ group, a $(CHCH_3CH_2O)_mL$ group wherein m is an integer varying between 1 and 10 or a $CH_2(CH_2)_{2-3}OH$ group;
X represents the unit of formula (I) provided that the oxygen atom of the carboxyl functional group of the unit (I) is linked to a hydrogen atom or to a primary or secondary carbon atom;
$R^{1'}$ represents a hydrogen atom, a $C_{1-22}$ hydrocarbon group optionally comprising one to three oxygen atoms and/or one to two nitrogen atoms and/or one sulfur atom, or, if $R^{1'}$ is linked to the oxygen atom of the carboxyl functional group of the unit (I), an alkaline metal ion;
p is an integer varying between 5 and 1000;
q is an integer varying between 0 and 500;
r is an integer varying between 0 and 1; and
T is a polymer terminating group;
optionally comprising at least one photo-catalyst; and
B) a shell surrounding said core formed by interfacial polymerization, by a phase separation process induced by polymerization or by coacervation.

For the sake of clarity, "microcapsule" or the similar, in the present invention includes both encapsulates such as core-shell systems (e.g. coacervates) or systems with a matrix morphology (e.g. extrudates or porous solid phases containing droplets of a liquid). By the terms "core-shell", it is meant that the oil phase is surrounded by a shell whereas "matrix morphology" means that the oil phase is dispersed in a matrix.

Preferably the microcapsule is a core-shell system.

According to a particular embodiment, the microcapsules is a non-diffusive microcapsule. For the sake of clarity, by the expression "non-diffusive" or the similar in the present invention it is meant that the shell or wall of the microcapsule is not permeable to the oil phase inside the microcapsule. By the expression "not permeable", it is meant that the release of the oil phase in absence of light shell is negligible or not perceivable (i.e. below the odor threshold).

By the terms "oil phase" it is meant a liquid or a solution, at 20° C. and 1 atm of pressure, which is capable of bringing a benefit or effect into its surrounding environment by the presence of an active agent such as, in particular, a perfuming, flavoring, cosmetic, skin caring, malodor counteracting, bactericide, fungicide, pharmaceutical or agrochemical ingredient, a diagnostic agent and/or an insect repellent or attractant.

Said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient, a diagnostic agent and/or as an insect repellent or attractant.

Preferably, said oil phase can be composed of a single compound or of a mixture of compounds wherein at least one of the said compounds possesses at least one property which renders it useful as perfuming, flavoring, cosmetic, skin caring, malodor counteracting, bactericide, fungicide, pharmaceutical or agrochemical ingredient and/or as an insect repellent or attractant. Even more preferably, said oil phase can be composed of a single compound or of a mixture of compounds wherein at least one of the said compounds possesses at least one property which renders it useful as perfuming, flavoring, and/or malodor counteracting.

Practically, the invention is carried out exactly in the same manner, independently of the exact nature of the active agent present in the oil phase. Therefore, it is understood that, even if the invention will be further illustrated herein below with a specific reference to "perfuming" ingredients, the below embodiments are also applicable to other active agent-containing oils (i.e. it is possible to replace the expression "perfuming" with "flavoring", "cosmetic", "skin caring", "malodor counteracting", "bactericide", "fungicide", "pharmaceutical", "agrochemical", "diagnostic agent", "insect attractant" or with "insect repellent" for instance).

For the sake of clarity, the terms "graft or linear polymer", or the similar, have the normal meaning understood by a person skilled in the art, i.e. that a linear polymer consists of a single continuous chain of repeating units and a graft polymer consists of a backbone with randomly distributed side chains of a different composition. In case of a linear polymer of formula (II), the unit of formula (I) is part of the backbone whereas, for a graft polymer of formula (III), the unit of formula (I) is part of the side chain grafted to the backbone. By the expression "backbone" it is meant the main chain of the polymer.

For the sake of clarity, by the expression "a benzenediyl functional group substituted in meta or para position", or similar, it is meant that the unit of formula (I) comprises a benzene-1,3-diyl functional group or a benzene-1,4-diyl functional group. Preferably, the unit of formula (I) comprises a benzenediyl functional group substituted in para position.

For the sake of clarity, by the expression "carboxyl functional group", it is meant an ester functional group or in a certain particular case, a carboxylic acid functional group.

For the sake of clarity, by the expression "primary or secondary carbon atom", or the similar, in the present invention it is meant that the oxygen atom of the carboxyl functional group of the unit of formula (I) is linked to a carbon atom having at least one hydrogen atom as a substituent or, in other words, the oxygen atom of the carboxyl functional group of the unit of formula (I) is linked to a CH or $CH_2$ group, e.g. the oxygen atom of the carboxyl functional group of the unit (I) is linked to a group of formula $(R^a)(R^b)CH$ or $(R^a)CH_2$ and the corresponding aldehyde or ketone formed upon exposure to light is of formula $(R^a)(R^b)C=O$ or $(R^a)CHO$.

The reference to the corresponding aldehyde or ketone is important since it is believed that upon exposure to light said photolabile polymer decomposes to form CO or $CO_2$ and an aldehyde or a ketone.

A linear polymer of formula (II) decomposes according to the following reaction wherein $R^2$ is a methyl group (herein shown for a secondary carbon atom):

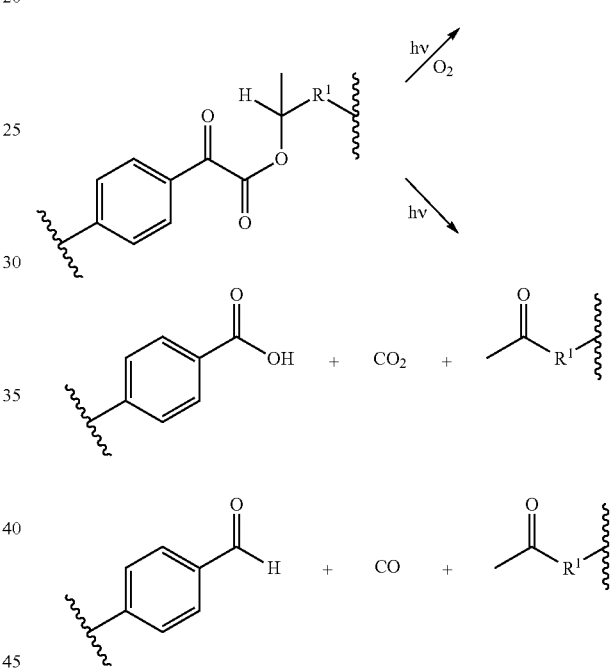

A graft polymer of formula (III) decomposes according to the following reactions wherein in reaction a) the hashed bond represents the bond between the unit of formula (I) and M, $R^{1'}$ is of formula $CH(R^a)(R^b)$ (herein shown for a secondary carbon atom); and wherein in reaction b) M is of formula $CH(R^c)(R^d)$, $R^{1'}$ is a hydrogen atom, and the hashed bond represents the bond between M and the backbone (herein shown for a secondary carbon atom):

a)

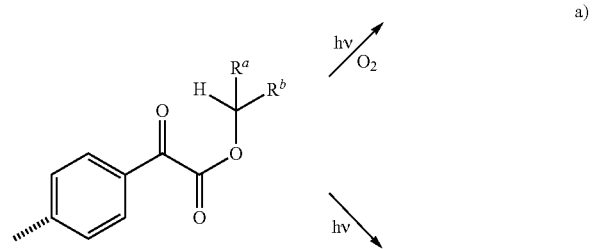

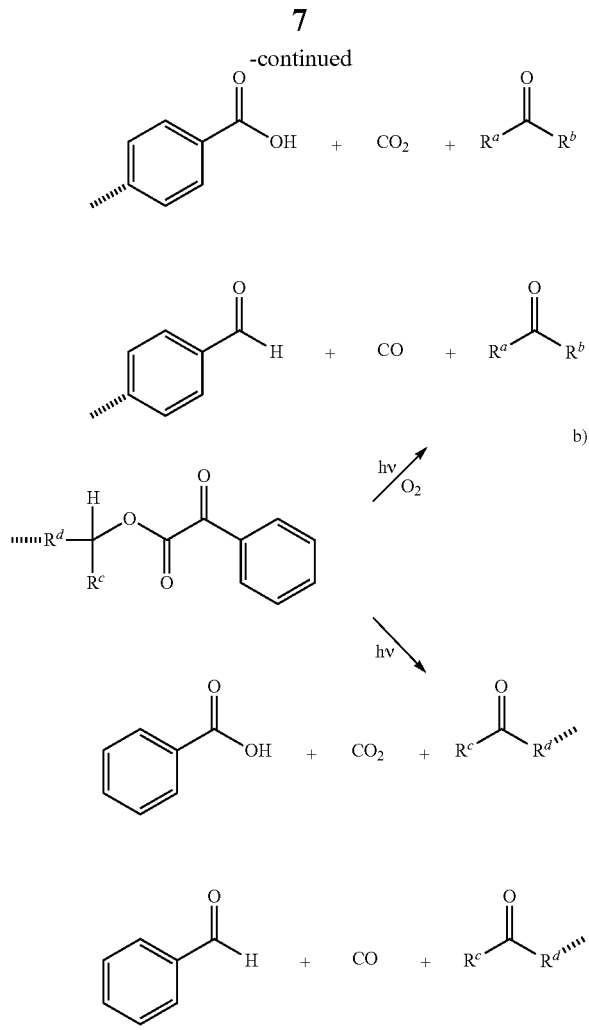

Depending on whether (ambient) oxygen reacts with the reaction intermediate generated upon exposure of a polymer of formula (II) or (III) to light, a gas being either CO or $CO_2$ or mixtures thereof is formed in addition to the above mentioned aldehyde or ketone.

In the presence or absence of oxygen, polymers of formula (III), wherein $R^{1'}$ is linked to the oxygen atom of the carboxyl functional group of the unit of formula (I) and represents a hydrogen atom, are believed to decompose upon exposure to light in an electron transfer reaction to form $CO_2$.

It is understood that by " . . . hydrocarbon group . . . " it is meant that said group consists of hydrogen and carbon atoms and can be in the form of aliphatic hydrocarbon, i.e. linear or branched saturated hydrocarbon (e.g. alkyl group), linear or branched unsaturated hydrocarbon (e.g. alkenyl or alkynyl group), saturated cyclic hydrocarbon (e.g. cycloalkyl) or unsaturated cyclic hydrocarbon (e.g. cycloalkenyl or cycloalkynyl), or can be in the form of aromatic hydrocarbon, i.e. aryl group, or can also be in the form of a mixture of said types of groups, e.g. a specific group may comprise a linear alkyl, a branched alkenyl (e.g. having one or more carbon-carbon double bonds), a (poly) cycloalkyl and an aryl moiety, unless a specific limitation to only one type is mentioned. Similarly, in all the embodiments of the invention, when a group is mentioned as being in the form of more than one type of topology (e.g. linear, cyclic or branched) and/or being saturated or unsaturated (e.g. alkyl, aromatic or alkenyl), it is also meant a group which may comprise moieties having any one of said topologies or being saturated or unsaturated, as explained above. Similarly, in all the embodiments of the invention, when a group is mentioned as being in the form of one type of saturation or unsaturation, (e.g. alkyl), it is meant that said group can be in any type of topology (e.g. linear, cyclic or branched) or having several moieties with various topologies.

For the sake of clarity, by the expression "containing one to three oxygen atoms and/or one to two nitrogen atoms and/or one sulfur atom", or the similar, in the present invention it is meant that the group, to which is made reference, may include functional groups such as for examples amines, thioethers, ethers, acetals, esters, aldehydes, ketones, amides, carboxylates, thiols or alcohols.

According to a particular embodiment of the invention, the invention's microcapsule is particularly useful when the oil phase comprises a perfuming oil, i.e. a single perfuming ingredient or a perfuming composition. A "perfuming ingredient" is a compound, which is of current use in the perfumery industry, i.e. a compound which is used as active ingredient in perfuming preparations or compositions in order to impart a hedonic effect. In other words, such a perfuming ingredient must be recognized by a person skilled in the art of perfumery as being able to impart or modify in a positive or pleasant way the odor of a composition, and not just as having an odor. For the sake of clarity, the definition of a perfuming ingredient is meant to include also compounds that do not necessarily have an odor but are capable of modulating the odor. For the sake of clarity, the definition of perfuming ingredient is meant to include also pro-perfumes, i.e. compounds which upon decomposition liberate a perfuming ingredient. In particular pro-perfumes are capable of releasing active compounds (e.g. perfuming ingredient) upon (slow) degradation and thus being capable of bringing a benefit or effect into the surrounding environment. The pro-perfumes degrade by cleavage of a covalent bond by hydrolysis (possibly induced by a change of pH), by oxidation, or by the action of enzymes, temperature or light to form the active compound. Preferably pro-perfume are photolabile and release a perfuming, flavoring or malodor counteracting compound upon exposure to light. Pro-perfumes capable of releasing active compounds upon (slow) degradation have been described in the prior art. A detailed description of the nature and type of these precursors is not required (and would not be exhaustive) as said precursors are well known to a person skilled in the art.

A "perfuming composition" is a mixture of compounds including at least two perfuming ingredients.

In general terms, these perfuming ingredients belong to chemical classes as varied as alcohols, thiols, lactones, aldehydes, ketones, esters, ethers, nitriles, terpenoids, nitrogenous or sulphurous heterocyclic compounds and essential oils, and said perfuming ingredients can be of natural or synthetic origin. Specific examples of such perfuming ingredients can be found in reference texts such as the book by S. Arctander, "Perfume and Flavor Chemicals", published by the author, Montclair (New Jersey, USA), 1969, or its more recent versions, or in other work of a similar nature, as well as in the abundant patent literature in the field of perfumery. They are well known to the person skilled in the art of perfuming consumer products, that is, of imparting a pleasant odor to a consumer product.

Such perfuming oil may also comprise solvents and/or adjuvants of current use in perfumery.

By "solvents of current use in perfumery" it is meant a material which is practically neutral from a perfumery point of view, i.e. that does not significantly alter the organoleptic properties of perfuming ingredients and is generally not miscible with water, i.e. possesses a solubility in water below 10%, or even below 5%. Solvents commonly used in perfumery suitable for the purpose of the invention, include for example dipropyleneglycol, diethyl phthalate, isopropyl myristate, benzyl benzoate, 2-(2-ethoxyethoxy)-1-ethanol or ethyl citrate, limonene or other terpenes, isoparaffins such as those known under the trademark Isopar® (origin: Exxon Chemical) or glycol ethers and glycol ether esters such as those known under the trademark Dowanol® origin: Dow Chemical Company).

By "adjuvants of current use in perfumery" it is meant ingredients capable of imparting additional added benefits such as a color, chemical stability, etc. A detailed description of the nature and type of adjuvants commonly used in a perfuming oil is not required (and would not be exhaustive) as said ingredients are well known to a person skilled in the art.

According to a particular embodiment of the invention, the oil phase of the invention's microcapsule can also comprise a non-polymeric gas-releasing compounds. Non-limiting examples of such compounds are 2-oxoacetates, butyrophenone or valerophenone, triazenes, 2,2'-azobis(2-methylpropionitrile), as well as organic carbonates.

The oil phase can be present in various amounts depending on its nature and/or on the strength of the aimed olfactive effect. Typically, the microcapsules comprise, based on the total microcapsule weight, from about 1% to about 99% by weight of oil phase. Preferably the microcapsules comprise from about 20% to about 96% by weight of oil phase.

According to a particular embodiment of the invention, the photolabile polymer upon decomposition generates a gas together with compounds or residues which are odorless.

For the sake of clarity, by the expression "odorless compound", or the similar, in the present invention it is meant that the compound (aldehyde or ketone) has a vapor pressure below 2.0 Pa, as obtained by calculation using the program EPI suite (4.0); EPA (US Environmental Protection Agency) and Syracuse Research Corporation (SRC), 2000. Preferably said vapor pressure is below 1.0 Pa, below 0.1 Pa, or even below 0.01 Pa, in other words, said corresponding compound is not a "perfuming" one. According to this embodiment, the generated aldehyde or ketone of the O—R$^{1'}$ moiety is an odorless compound, provided that the group R$^{1'}$ derived from a perfuming aldehyde or ketone is excluded.

According to another particular embodiment of the invention, the photolabile polymer upon decomposition generates a gas together with a perfuming aldehyde or ketone. An exhaustive list of said perfuming aldehydes or ketones would be too long and tedious to be given, and a person skilled in the art of perfumery knows exactly what is meant and encompassed by the expression "perfuming aldehyde and ketones". The definition of perfumery ingredient is provided above.

According to a particular embodiment of the invention, the photolabile polymer is a linear polymer of formula (II).

According to any embodiment of the invention, the photolabile polymer comprising an sa-ketoester group is a linear polymer of formula (II) wherein R$^1$ represents a C$_{1-8}$ aliphatic hydrocarbon group.

According to any embodiment of the invention, said R$^1$ represents a C$_{1-6}$ aliphatic hydrocarbon group.

According to any embodiment of the invention, said R$^1$ represents a C$_{1-6}$ linear alkanediyl group, a C$_{3-6}$ branched alkanediyl group.

According to any embodiment of the invention, preferred photolabile polymers of formula (II) are those wherein R$^1$ represents a group selected from the group consisting of methanediyl, ethanediyl, 2-methylethanediyl, propanediyl, 2-methylpropanediyl, n-butadiyl and pentanediyl. Even more preferably R$^1$ represents a group selected from the group consisting of methanediyl, ethanediyl and 2-methylethanediyl.

According to a particular embodiment of the invention, the photolabile polymer is a graft polymer of formula (III).

According to a particular embodiment of the invention, the photolabile polymer is a polymer formula

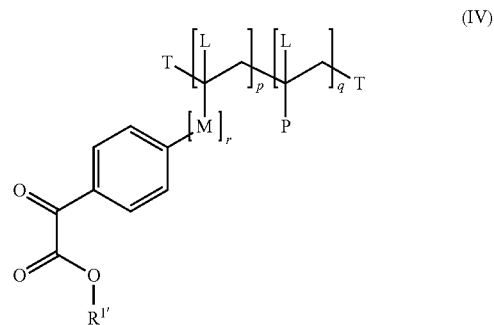

(IV)

wherein

L is a hydrogen atom or a methyl group;

M represents a C$_{1-8}$ aliphatic hydrocarbon group optionally comprising one or two oxygen atoms and/or one nitrogen atom;

P represents, independently from each other, a OR$^3$ group; a COOR$^3$ group, a COOCH$_2$C$_6$H$_5$ group, a COOC$_6$H$_5$ group, a C$_6$H$_5$ group, a C$_6$H$_4$COOR$^3$ group, a C$_6$H$_4$OH group, a OC(=O)R$^3$ group, a CON(R$^3$)$_2$ group, a CONLR$^3$ group, a 2-oxopyrrolidin-1-yl group or a 2-oxoazepan-1-yl group, wherein R$^3$ represents a hydrogen atom, a C$_{1-18}$ alkyl group, a (CH$_2$CH$_2$O)$_m$L group, a (CHCH$_3$CH$_2$O)$_m$L group wherein m is an integer varying between 1 and 10 or a CH$_2$(CH$_2$)$_{2-3}$OH group;

R$^{1'}$ represents a hydrogen atom, a C$_{1-22}$ hydrocarbon group optionally comprising one to three oxygen atoms and/or one to two nitrogen atoms and/or one sulfur atom provided that said group is linked to the oxygen atom of the carboxyl functional group through a primary or secondary carbon atom;

p is an integer varying between 5 and 1000;

q is an integer varying between 0 and 500;

r is an integer varying between 0 and 1; and

T is a polymer terminating group.

According to a particular embodiment of the invention, the photolabile polymer is a polymer formula

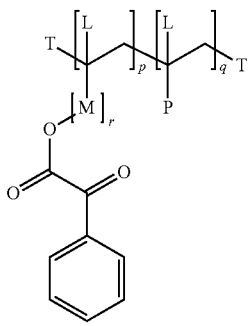

(V)

wherein
M represents a $C_{1-8}$ aliphatic hydrocarbon group optionally comprising one or two oxygen atoms and/or one nitrogen atom provided that M is linked to the oxygen atom of the carboxyl functional group through a primary or secondary carbon atom;

P represents, independently from each other, a $OR^3$ group; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a $CONLR^3$ group, a 2-oxopyrrolidin-1-yl group or a 2-oxoazepan-1-yl group, wherein $R^3$ represents a hydrogen atom, a $C_{1-18}$ alkyl group, a $(CH_2CH_2O)_mL$ group, a $(CHCH_3CH_2O)_mL$ group wherein m is an integer varying between 1 and 10 or a $CH_2(CH_2)_{2-3}OH$ group;

p is an integer varying between 5 and 1000;
q is an integer varying between 0 and 500;
r is an integer varying between 0 and 1 provided that r is 0 when L is a hydrogen atom; and
T is a polymer terminating group.

According to any embodiment of the invention, the photolabile polymer comprising an sa-ketoacid or sa-ketoester group is a graft polymer wherein M represents a group of formula a):

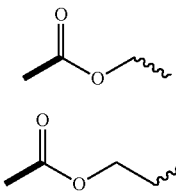

a)

wherein the wavy line indicates the location of the bond between said M and X, and the bold line indicates the location of the bond between said M and the unit of formula $[C(L)CH_2]_p$, and wherein Y represents an oxygen atom, or a carboxyl functional group, $R^4$ represents $C_{1-7}$ aliphatic hydrocarbon group and r as the same meaning as above providing that r is equal to 0 only when Y is a carboxyl functional group.

According to any embodiment of the invention, $R^4$ represents $C_{1-7}$ linear alkanediyl group, a $C_{3-7}$ branched alkanediyl group, preferably $C_{1-3}$ linear alkanediyl group.

According to any embodiment of the invention, the photolabile polymer comprising an sa-ketoacid or sa-ketoester group is a graft polymer wherein M represents a group selected from the group consisting of formulae b) to d):

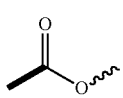

b)

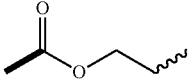

c)

d)

wherein the wavy line indicates the location of the bond between said M and X and the bold line indicates the location of the bond between said M and the unit of formula $[C(L)CH_2]_p$. Preferably, M represents a group of formula d) wherein the wavy line indicates the location of the bond between said M and X and the bold line indicates the location of the bond between said M and the unit of formula $[C(L)CH_2]_p$.

According to any embodiment of the invention, the photolabile polymer comprising an α-ketoacid or α-ketoester group is a graft polymer wherein $R^{1'}$ represents a hydrogen atom or a $C_{2-16}$ hydrocarbon group optionally comprising one to three oxygen atoms and/or one nitrogen atom.

According to any embodiment of the invention, $R^{1'}$ represents a hydrogen atom or a $C_{2-10}$ hydrocarbon group optionally comprising one to three oxygen atoms and/or one or two nitrogen atoms.

According to any embodiment of the invention, $R^{1'}$ represents a hydrogen atom or a $C_{2-10}$ alkyl group optionally comprising one to three oxygen atoms and/or one or two nitrogen atoms.

According to any embodiment of the invention, preferred photolabile polymers of formula (III) or (IV) are those wherein $R^{1'}$ represents a group selected from the group consisting of, hydrogen, methyl, ethyl, propyl, isopropyl, 2-methylpropyl, n-butyl, 2-butyl, pentyl, cyclopentyl, hexyl, cyclohexyl, 2-mesityl, 2-ethoxy-2-oxoethyl, 2-methoxy-2-oxoethyl, 2-isopropoxy-2-oxoethyl, 2-oxopropyl, 3-ethoxy-3-oxopropyl, 3-methoxy-3-oxopropyl, 3-isopropoxy-3-oxopropyl, 3-oxobutyl, 4-ethoxy-4-oxobutyl, 4-methoxy-4-oxobutyl, 4-isopropoxy-4-oxobutyl and 3,3-dimethyl-2-oxobutyl. Even more preferably $R^{1'}$ represents a group selected from the group consisting of hydrogen, methyl, ethyl and isopropyl. Even more preferably, $R^{1'}$ represents a group selected from the group consisting of hydrogen and methyl group.

According to a particular embodiment of the invention, the photolabile polymer comprising an α-ketoacid or α-ketoester group is a graft polymer wherein P represents, independently from each other, a $OR^3$ group; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a $CONHR^3$ group, a 2-oxopyrrolidin-1-yl group or a 2-oxoazepan-1-yl group, wherein $R^3$ represents a hydrogen atom, a $C_{1-4}$ alkyl group a $(CH_2CH_2O)_mL$ group, a $(CHCH_3CH_2O)_mL$ group wherein m is an integer varying between 1 and 10 or a $CH_2(CH_2)_{2-3}OH$ group. More preferably P represents, independently from each other, a $OR^3$; a $COOR^3$ group, a $COOCH_2C_6H_5$ group, a $COOC_6H_5$ group, a $C_6H_5$ group, a $C_6H_4COOR$ group, a 2-oxopyrrolidin-1-yl group or a 2-oxoazepan-1-yl group wherein $R^3$ represents a hydrogen atom or a $C_{1-4}$ alkyl group. More preferably $R^3$ represents a methyl, n-butyl, n-propyl or isopropyl group.

According to a particular embodiment of the invention, the photolabile polymer comprising an α-ketoacid or α-ketoester group is a graft polymer wherein P represents, independently from each other, a $OR^3$; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a $CONHR^3$ group, a 2-oxopyrrolidin-1-yl group or a 2-oxoazepan-1-yl group, wherein $R^3$ represents a $C_{5-18}$ alkyl group. More preferably P represents $OR^3$; a $COOR^3$ group, a $COOCH_2C_6H_5$ group, a $COOC_6H_5$ group, a $C_6H_5$ group, a $C_6H_4COOR$ group, a 2-oxopyrrolidin-1-yl group or a 2-oxoazepan-1-yl group, wherein $R^3$ represents a $C_{5-18}$ alkyl group. Even more preferably $R^3$ represents a $C_{8-14}$ alkyl group.

According to any embodiment of the invention, P represents, independently from each other, a $OR^3$ group; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$ group, a 2-oxopyrrolidin-1-yl group or a 2-oxoazepan-1-yl group, wherein $R^3$ represents a hydrogen atom, a $C_{1-18}$ alkyl group or a $CH_2(CH_2)_{1-3}OH$ group. By the term "P represents, independently from each other", it is meant than when q is superior at 1, P groups could be different.

According to any embodiment of the invention, P represents, independently from each other, a $OR^3$ group; a $COOR^3$ group and a $C_6H_5$ group wherein $R^3$ represents a hydrogen atom, a $C_{1-4}$ alkyl group or a $CH_2CH_2OH$ group.

According to any embodiment of the invention, the polymer terminating groups can be of various chemical structures and are well known by a person skilled in the art. Typical examples comprise a hydrogen atom or hydroxyl group or a halogen atom, a methyl group or an ethylene group. If q>1, then the polymer of formula (III) is a co-polymer of the random or the block type.

According to any embodiment of the invention, the photolabile polymer comprising an α-ketoacid or α-ketoester group generates a gas upon exposure to light at a wavelength comprised between 450 and 320 nm, preferably between 400 and 320 nm and even more preferably between 380 and 340 nm.

According to any embodiment of the invention, the photolabile polymer comprising an α-ketoacid or α-ketoester group is characterized by a molecular weight comprised between 300 g/mol and 100000 g/mol, preferably comprised between 500 g/mol and 20000 g/mol and even more preferably comprised between 1000 g/mol and 10000 g/mol.

According to any embodiment of the invention, the invention's photolabile co-polymers IV or V are characterized by a solubility parameter comprised between 15 and 30 $(MPa)^{0.5}$.

For the sake of clarity the "solubility parameters" of the monomers composing the photolabile co-polymers IV or V are defined as the square root of the cohesive energy density, obtained according to the method of Marrero and Gani using the ICAS 15.0, ProPred Component Property Prediction software. The solubility parameter of the co-polymer is then calculated from the solubility parameters of the corresponding monomers by taking into account the mole fraction of each monomer in the final co-polymer.

The following table lists the solubility parameters δ for a monomer of the invention's photolabile polymers IV or V.

| Monomers according to the invention | Solubility parameter δ $(MPa^{0.5})^a$ |
|---|---|
| Ethyl-2-oxo-2-(4-vinylphenyl)acetate | 21.09 |
| Methyl-2-oxo-2-(4-vinylphenyl)acetate | 21.25 |
| Isopropyl-2-oxo-2-(4-vinylphenyl)acetate | 20.48 |
| 2-Phenylethyl 2-oxo-2-(4-vinylphenyl)acetate | 22.46 |
| 2-(2-Oxo-2-phenylacetoxy)ethyl methacrylate | 22.24 |

$^a$Data obtained according to the method of Marrero and Gani using the ICAS 15.0, ProPred Component Property Prediction software.

The following table lists the solubility parameters δ for a series of co-monomers.

| Co-monomers according to the invention | Solubility parameter δ $(MPa^{0.5})^a$ |
|---|---|
| Methyl methacrylate | 17.99 |
| Methyl acrylate | 18.74 |
| Methacrylic acid | 21.40 |
| Acrylic acid | 22.15 |
| 2-Hydroxyethyl methacrylate | 18.67 |
| Styrene | 19.53 |
| 4-Vinylbenzoic acid | 21.39 |
| 2-Oxoethyl methacrylate | 20.90 |
| Vinyl acetate | 18.29 |
| N-vinyl pyrrolidinone | 20.38 |
| n-Butyl Methacrylate | 17.53 |
| n-Butyl Acrylate | 18.28 |

$^a$Data obtained according to the method of Marrero and Gani using the ICAS 15.0, ProPred Component Property Prediction software.

As an example, the co-polymer poly(2-(2-oxo-2-phenylacetoxy)ethyl methacrylate)-co-poly(2-hydroxyethyl methacrylate)-co-poly(butyl methacrylate) (Polymer 7 prepared in Example 1) consists of 54 mol % of n-butyl methacrylate (δ=17.53 $MPa^{0.5}$), 7 mol % of 2-hydroxyethyl methacrylate (δ=18.67 $MPa^{0.5}$) and 39 mol % of 2-(2-oxo-2-phenylacetoxy)ethyl methacrylate (δ=22.24 $MPa^{0.5}$). The final co-polymer has a solubility parameter of 19.45 $MPa^{0.5}$. Upon exposure to daylight, the gas is generated forming a new monomer unit (2-oxoethyl methacrylate, δ=20.90 $MPa^{0.5}$) in the co-polymer. The resulting co-polymer has (after quantitative gas generation) a solubility parameter of 18.92 $MPa^{0.5}$.

As an example, the co-polymer poly(ethyl 2-oxo-2-(4-vinylphenyl)acetate)-co-poly(styrene) (Polymer 4 prepared in Example 1) consists of 58 mol % of styrene (δ=19.53 $MPa^{0.5}$) and 42 mol % of ethyl-2-oxo-2-(4-vinylphenyl) acetate (δ=21.09 $MPa^{0.5}$). The final co-polymer has a solubility parameter of 20.19 $MPa^{0.5}$.

The photolabile polymer can be included into the microcapsules in various amounts depending on its nature and the speed of release of the oil phase which is aimed. Typically, the microcapsules comprise, based on the total microcapsule weight, from about 1% to about 99% (or even 90%) by weight, of photolabile polymer. Preferably the microcapsules comprise from about 5% to about 80% of photolabile polymer, preferably from 10% to about 50% of photolabile polymer, even more preferably from 15% to about 30% of photolabile polymer.

According to any embodiment of the invention, several gas-releasing photolabile polymers can be used simultaneously as mixtures, all of which can release the same type of gas or different types of gases.

It is believed that upon exposure to light, the photolabile polymer generates a gas which, causes an increase in the internal pressure leading to the release of the oil phase. The formation of the gas in the core of the capsule is considerably faster than the diffusion of the gas through the polymer wall. The increase in internal pressure might result in an extension or breaking of the microcapsule shell or wall. The extension (swelling) of the capsule shell should make the capsule more diffusive towards the outside and thus facilitate the release of the encapsulated oil phase. Depending on the chemical structure of the capsule shell and on the speed of gas formation, the extension of the capsule shell might finally lead to a complete breaking of the capsule shell and thus allow the oil phase to leak out. All these parameters can be easily optimized by a person skilled in the art considering the thickness of the walls its chemical nature and the loading of photo-labile polymer in the capsules as well as the desired speed of release.

Photolabile polymers of the present invention can be prepared by esterification or transesterification and/or by Friedel-Crafts reaction. Photolabile polymers of formula (II) can be prepared for example by esterification of a 2-oxo-2-phenylacetic acid with a 2-halideethan-1-ol, followed by Friedel-Crafts reaction. Photolabile polymers of formula (III) can be prepared for example by esterification of 2-oxo-2-phenylacetic acid with 2-hydroxyethyl (meth)acrylate followed by polymerization or co-polymerization. Alternatively, said polymers can also be obtained by esterification of a 2-oxo-2-phenylacetic acid with a polyvinyl alcohol or with a poly(2-hydroxyethyl (meth)acrylate) unit of a preformed homo- or co-polymer, or by Friedel-Crafts reaction of ethyl 2-chloro-2-oxoacetate with a polystyrene unit of a preformed homo- or co-polymer. Transesterification and/or Friedel-Crafts reaction could be stopped before full conversion which leads to polymers having different P group when the starting polymer is a co-polymer.

The efficiency of generating a gas from said photolabile polymer upon exposure to the light can be influenced by energy transfer via a photo-catalyst. Said photo-catalyst can act via various mechanisms such as by photosensitation, photocatalysis or by photo-assisted catalysis. As defined by the International Union of Pure and Applied Chemistry (IUPAC) in Pure and Applied Chemistry, 2006, vol. 79, pages 293-465, the term "photosensitation" stands for a "photochemical or photophysical alteration" occurring in one molecular entity as a result of initial absorption of radiation by another molecular entity called a "photosensitizer". "Photocatalysis" means a "change in the rate of a chemical reaction or its initiation under the action of ultraviolet, visible, or infrared radiation in the presence of a substance—the photocatalyst—that adsorbs light and is involved in the chemical transformation of the reaction partners". Similarly, the term "photo-assisted catalysis" has been defined by the same source as a "catalytic reaction involving production of a catalyst by absorption of ultraviolet, visible or infrared radiation".

The core A) of the microcapsule according to the invention optionally also comprises at least one photo-catalyst. The choice of a suitable photo-catalyst depends on the structure of the gas-generating photolabile polymer and on the medium in which the photoreaction is supposed to take place. Said photo-catalysts are therefore of various chemical structures and are well known by a person skilled in the art. Typical examples are found in the literature (e.g. M. Wainwright, "Photosensitizers in Biomedicine", John Wiley & Sons, Chichester, 2009, or G. K. Castello (Ed.), "Handbook of Photocatalysts: Preparation, Structure and Applications", Materials Science and Technologies Series, Nova Science Publishers, New York, 2010, or in other work of a similar nature, as well as in the abundant patent literature in the field of photosensitation or photocatalysis).

Non-limiting examples of compounds that might be suitable as photo-catalysts in some cases (e.g. for the use of α-ketoacids) comprise dyes, such as methylene blue, rose bengal, riboflavin or rhodamine B, as well as different forms of titanium dioxide.

Said photo-catalyst can be included in various amounts depending on its nature and the speed of release of the oil phase which is aimed. Typically, the microcapsules comprise, based on the total microcapsule weight, from about 0.01% to about 50% by weight, of a photo-catalyst. Preferably the microcapsules comprise from about 1% to about 20% by weight of photo-catalyst.

The component B) of the microcapsules according to the invention is a shell that can be obtained by a variety of processes.

According to any embodiment of the invention, the shell is preferably based on aminoplast, polyamide, polyester, polyurea or polyurethane resins or a mixture thereof. Said resins and shells are well known to a person skilled in the art.

According to any embodiment of the invention, such a shell is preferably obtained by a phase separation process induced by polymerization, by interfacial polymerization, by coacervation or altogether. Such processes have been described in the prior art. Such a process can, for example, be based on amino resins produced by the polycondensation of an aldehyde (e.g. formaldehyde, 2,2-dimethoxyethanol, glyoxal, glyoxylic acid or glycolaldehyde and mixtures thereof) with an amine, namely urea, benzoguanamine, glycoluryl, melamine, methylol melamine, methylated methylol melamine, guanazole and the like, as well as mixtures thereof. Examples for suitable ureas are dimethylol urea, methylated dimethylol urea, urea-resorcinol, and mixtures thereof.

Some of the seminal literature related to the encapsulation of perfumes by polycondensation of amino resins, namely melamine based resins, with aldehydes is represented by articles such as those published by K. Dietrich et al. in Acta Polymerica, 1989, vol. 40, pages 243, 325 and 683, as well as 1990, vol. 41, page 91. Such articles already describe the various parameters affecting the preparation of such core-shell microcapsules following prior art methods that are also further detailed and exemplified in the patent literature. U.S. Pat. No. 4,396,670, to the Wiggins Teape Group Limited is a pertinent early example of the latter. Since then, many other authors and creators have enriched the literature in this field and it would be impossible to cover all published developments here, but the general knowledge in this type of encapsulation is very significant. More recent publications of pertinence, which also address the suitable uses of such microcapsules, are represented for example by the article of H. Y. Lee et al. in Journal of Microencapsulation, 2002, vol. 19, pages 559-569, international patent publication WO01/41915 or yet the article of S. Bône et al. in Chimia, 2011, vol. 65, pages 177-181.

The polycondensation of an aldehyde with an amine or an amino resin leads to shells or walls consisting of highly cross-linked resins known as thermoset resins (aminoplast resins). Suitable alkylolated polyamines for the microcapsules according to the invention encompass mixtures of mono- or polyalkylolated polyamines, which in turn may be partially alkylated with alcohols having from 1 to 6 methylene units, and also encompass mono- or polymethylolmelamine and/or mono- or polymethylolurea precondensates, such as those commercially available under the trademark Urac® (origin: Cytec Technology Corp.), Cymel® (origin: Cytec Technology Corp.), Urecoll® or Luracoll® (origin: BASF).

Other suitable amino resins from the mixtures of mono- or polyalkylolated polyamines can be obtained by polycondensation of an aldehyde such as 2,2-dimethoxyethanal, glyoxal, glyoxylic acid or glycolaldehyde and mixtures thereof, and an amine, as described in WO 2011/161618. Non-limiting examples of polyalkylolated polyamines from the polycondensation with 2,2-dimethoxyethanal comprise poly [N-(2,2-dimethoxy-1-hydroxy)] polyamines, mono- and di-[N-(2,2-dimethoxy)-1-hydroxy)] urea, mono-, di-, tri-, and/or tetra-[N-(2,2-dimethoxy)-1-hydroxy)] melamine, tetra-[N-(2,2-dimethoxy)-1-hydroxy)] glycouryl or di-[N-(2,2-dimethoxy)-1-hydroxy)] benzoguanidine. Non-limiting examples of polyalkylolated polyamines from the polycondensation with glyoxal comprise poly[N-(2-hydroxyacetaldehyde)] polyamines, mono- and di-[N-(2-hydroxyacetaldehyde)] urea, mono-, di-, tri-, and/or tetra-[N-(2-hydroxyacetaldehyde)] melamine, tetra-[N-(2-hydroxyacetaldehyde)] glycouryl or di-[N-(2-hydroxyacetaldehyde)] benzoguanidine. Non-limiting examples of polyalkylolated polyamines from the polycondensation with glyoxylic acid comprise poly[N-(2-hydroxyacetic acid)] polyamines, mono- and di-[N-(2-hydroxyacetic acid)] urea, mono-, di-, tri-, and/or tetra-[N-(2-hydroxyacetic acid)] melamine, tetra-[N-(2-hydroxyacetic acid)] glycouryl or di-[N-(2-hydroxyacetic acid)] benzoguanidine. Non-limiting examples of polyalkylolated polyamines from the polycondensation with glycolaldehyde comprise poly[N-(ethane-1,2-diol)] polyamines, mono- and di-[N-(ethane-1,2-diol)] urea, mono-, di-, tri-, and/or tetra-[N-(ethane-1,2-diol)] melamine, tetra-[N-(ethane-1,2-diol)] glycouryl or di-[N-(ethane-1,2-diol)] benzoguanidine.

According to an embodiment of the invention, core-shell microcapsules are obtained by interfacial polymerization, in which the core is encapsulated into a crosslinked polyurea or polyurethane shell or wall formed by reaction of an amino resin, a polyamine or polyol with at least one polyisocyanate.

A polyurea microcapsule shell or wall is formed when a polyamine or an amino resin is used. Particularly efficient polyamines are water soluble guanidine salts and/or guanidine and/or amino resins such as those described above. By "water soluble guanidine salt" it is meant a salt soluble in water and resulting from the reaction of guanidine with an acid. One example of such salts is guanidine carbonate.

In the case where a polyol is used as the cross-linker, a polyurethane microcapsule shell or wall is formed. As polyol, glycerol is preferred.

The use of specific proportions of polyisocyanate versus polyamine or polyol is advantageous. Therefore, preferably, for each mole of isocyanate group, 1 to 10, preferably 2 to 5 moles of amine or alcohol groups are present. Accordingly, there is added an excess of the cross-linking agent.

When a polyisocyanate compound is reacted with an amino resin, e.g. obtained by a phase separation process as described above, a polyamine or a polyol, any polyisocyanate is suitable for the reaction, but a polyisocyanate comprising at least two isocyanate groups or at least three isocyanate groups is preferred. Low volatility polyisocyanate molecules are preferred because of their low toxicity. In particular, the polyisocyanate can advantageously be selected from the group consisting of a trimer of hexamethylene diisocyanate, a trimer of isophorone diisocyanate or xylylene diisocyanate or a Biuret of hexamethylene diisocyanate or a trimer of xylylene diisocyanate with trimethylolpropane (known with the tradename of Takenate®, origin: Mitsui Chemicals), among which a trimer of xylylene diisocyanate with trimethylolpropane and a Biuret of hexamethylene diisocyanate are even more preferred.

For the sake of clarity, by the expression "dispersion", in the present invention, it is meant a system in which particles are dispersed in a continuous phase of a different composition, and this term specifically includes a suspension or an emulsion.

A polymeric stabilizer can be used to prevent the microcapsules from agglomerating, thus acting as a protective colloid which is added to the monomer mixture, intended to form the shell, prior to polymerization. For the sake of clarity, in the present context by the expression "stabilizer", or similar, it is understood the meaning usual in the art, i.e. a compound that is capable of, or is added to, stabilize the system, e.g. to prevent aggregation or agglomeration of the microcapsules, for example in the consumer product application or during the process for the microcapsule preparation. The use of said stabilizer is standard knowledge to the person skilled in the art.

For the purpose of the present invention, said stabilizer can be an ionic or non-ionic surfactant or a colloidal stabilizer. The exact nature of such stabilizers is well known to a person skilled in the art. As non-limiting examples one may cite the following stabilizers: non-ionic polymers such as polyvinyl alcohol (Mowiol 18-88, Origin: Fluka), cellulose derivatives such hydroxyethyl cellulose or carboxymethyl cellulose such as Ambergum™ 1221 (origin: Aqualon Hercules), polyethylene oxide, co-polymers of polyethylene oxide and polyethylene or polypropylene oxide, co-polymers of alkyl acrylates and N-vinylpyrrolidone; ionic polymers such as acrylic co-polymers of acrylamide and acrylic acid such as Alcapsol® 144 (origin: Ciba), e.g. acid/acrylamide co-polymers produced from a monomer mixture of acrylic acid and acrylamide wherein the acrylic acid content is in the range of from 20 to 80%, acid anionic surfactants (such as sodium dodecyl sulfate), acrylic co-polymers bearing a sulfonate group (such as sodium poly(styrene sulfonate), and co-polymers of vinyl ethers and maleic anhydride.

Optionally, the microcapsules may be coated with a cationic co-polymer. The cationic polymer allows partial or complete neutralization of the negative electrical charge borne by the microcapsules, or even the conversion of the negatively-charged microcapsules into positively-charged microcapsules. To this effect, according to the invention, preferred cationic polymers comprise cationic polyacrylates and acrylamides such as Salcare® SC60 (origin: BASF), cationic cellulose derivatives, such as those available under the trademark Ucare® (origin: Amerchol), and quaternized guar gums available under the trademark Jaguar® (origin: Rhodia). Other cationic compounds that can be used include the polyquaternium compounds, all which have a plurality of quaternary ammonium groups, or polymeric species such as diallyl dimethyl ammonium chloride/acrylamide polymers such as those available under the trade name Merquat® (origin: Nalco).

According to any embodiment of the invention, if the oil phase to be encapsulated by a polymerization process is hydrophobic (e.g. with the logarithm of its octanol/water partition coefficient (log P)>1, preferably >2), it will be included in the water-immiscible phase, whereafter the two phases are mixed by high shear mixing to form an oil-in-water emulsion. In this emulsion, the polymerization will take place at the interface between the two phases. Thus, the oil droplets will be surrounded by the microcapsule shell formed by the polymerization process.

According to any embodiment of the invention, the average size of the microcapsules may range between 1 micrometer to 100 micrometers, or even more, depending on the mixing shear stress applied to the system during microcapsule formation. The selection of the most appropriate range and distribution of size depends on the application for which the microcapsules are intended, and can be controlled and adjusted by the skilled person as a function of the latter. In a general manner the average size of the microcapsules according to the invention ranges between 1 micrometer and 600 micrometers and, more preferably, comprises a range of 10 to 200 micrometers.

The phase separation process induced by polymerization and the interfacial polymerization process described above essentially convert emulsions, consisting of a dispersed oil phase, containing the photolabile polymer and, optionally, the photo-catalyst to be encapsulated and a continuous water phase, into a dispersion of solid beads consisting of a core surrounded by a shell, whose permeability depends on a number of factors, including the extent of cross-linking, and/or the thickness of the shell. A person skilled in the art is able to easily find optimal factors and conditions to obtain non-diffusive capsules as required by the present invention.

According to any embodiment of the invention, the invention's microcapsules obtained either by phase separation polycondensation or by interfacial polymerization have a shell thickness varying between 10 to 1000 nm, preferably between 20 and 500 nm, even more preferably between 25 and 350 nm. As an example, the capsule's shell thickness can be determined by atomic force microscopy (AFM) or scanning electron microscopy (SEM).

According to any embodiment of the invention, the microcapsules of the present invention may be characterized by a nominal shell to core mass ratio lower than 40%, preferably lower than 20% and, most preferably, lower than 10%, the invention thus providing thin and frangible shells that allow the diffusion of the fragrance molecules resulting from the degradation of the photolabile polymer.

The nominal shell to core mass ratio depends on the amount of amino resin or polyamine or polyol and/or polyisocyanate used for the preparation of the microcapsules (and thus the shell thickness of the capsule) and which has a strong influence on the performance of the delivery system. An optimum value to reach a maximum of capsule stability and the best release performance has to be reached. Specific examples according to the invention are presented further on. As an example, the nominal shell to core mass ratio can vary from 0.4 to 0.01, preferably from 0.3 to 0.02, most preferably from 0.10 to 0.03.

The microcapsules of the present invention are provided in the form of aqueous slurries, having typically 20 to 55% of solid content, where the term "solid content" is relative to the total weight of the microcapsules. Alternatively, such slurries may be spray-dried in a generally known manner to provide powder products.

The slurry may contain formulation aids, such as stabilizing and viscosity control hydrocolloids, biocides, and, as the case may be, formaldehyde scavengers.

The aqueous phase can also advantageously comprise hydrophilic inorganic particles such as silica particles or titanium oxide, in order to adjust the density of the microcapsules. By doing so, the density of the microcapsules can be brought to a value similar to that of the end product into which it is intended to incorporate them and therefore the microcapsules are maintained homogeneously suspended and dispersed in such liquid products. This is particularly advantageous in perfuming microcapsules because the specific gravity of the perfuming ingredients is usually lower than 1 g/mL.

The microcapsules according to the invention protect the oil phase against premature degradation during storage in the application formulation and increase the deposition of the oil phase on the target substrate once the latter is treated with the consumer product.

According any embodiment of the invention, one may use the microcapsules of the present invention as a mixture with a free oil phase and/or with other microcapsules or other types of delivering technologies of the prior-art. Other microcapsules used in combination with those of the present invention can have a diffusive or non-diffusive shell.

Furthermore, the invention's microcapsules can also be advantageously used in all the fields of modern perfumery, i.e. fine or functional perfumery, to positively impart or modify the odor of a consumer product into which said invention's microcapsules are added. Consequently, another object of the present invention is represented by a perfuming consumer product comprising, i) as a perfuming ingredient, at least one invention's microcapsule, as defined above; and ii) optionally a free perfume oil.

Such consumer product may be a solid or a liquid product. According to a particular embodiment, liquid products are preferred.

For the sake of clarity, by "free perfume oil" it is meant a perfume oil, e.g. as defined above, which is not encapsulated or part the invention microcapsules.

For the sake of clarity, by "consumer product" it is meant a consumer product which is typically perfumed and which is expected to deliver at least a perfuming effect, in other words it is a perfumed consumer product.

For the sake of clarity, it has to be mentioned that, by "perfuming consumer product" it is meant a consumer product which is expected to deliver at least a pleasant perfuming effect to the surface to which it is applied (e.g. skin, hair, textile, or hard surface). In other words, a perfuming consumer product according to the invention is a perfumed consumer product which comprises a functional formulation, as well as optionally additional benefit agents, corresponding to the desired consumer product, e.g. a detergent or an air freshener, and an olfactive effective amount of the microcapsules according to the present invention. It goes without saying that such a consumer product may also contain non-encapsulated perfume, i.e. perfume ingredients in free form.

The nature and type of the constituents of the consumer product do not warrant a more detailed description here, which in any case would not be exhaustive, the skilled person being able to select them on the basis of his general knowledge and according to the nature and the desired effect of said product.

Non-limiting examples of consumer products in which the microcapsules according to the invention can be used advantageously include perfumes, colognes or after-shave lotions; fabric care products, such as a liquid or solid detergents, fabric softeners or refreshers, ironing waters, tissues or other paper or cellulose based products such as nappies, and bleaches or home care products, including window and kitchen cleaners; body and hair care products (e.g. a shampoos, coloring preparations, conditioners and hair sprays), cosmetic preparations (e.g. creams, body deodorants or antiperspirants), or skin-care products (e.g. a perfumed soap, shower or bath mousse, oils or gels, or a hygiene product); an air care product, such as an air freshener or a "ready to use" powdered air freshener; or a home care product, such as a wipe, a dish detergent or hard-surface detergent.

As anticipated above, the invention's composition can be advantageously used for bringing a benefit to consumer products, such as its perfuming effect. Because some of the compounds of the oil phase described above can also have flavoring, cosmetic, skin caring, malodor counteracting, bactericide, fungicide, pharmaceutical, agrochemical, insect attractant or repellent properties, it is evident that the invention's microcapsules can also be used in formulations serving for flavoring, cosmetic, skin caring, malodor counteracting, bactericide, fungicide, pharmaceutical, agrochemical, insect attractant or repellent purposes. Indeed, said microcapsules, possess several other properties that make them particularly suitable for this purpose.

The proportions in which the microcapsules according to the invention can be incorporated into the various aforementioned consumer products vary within a wide range of values. These values are dependent on the nature of the article to be perfumed and on the desired organoleptic effect as well as the nature of the co-ingredients in a given consumer product. Typically, the consumer products comprise, based on the total consumer product weight, from about 0.01% to about 80% by weight, of microcapsules according to the present invention. Preferably the consumer products comprise from about 0.01% to about 30% of microcapsules. More preferably the consumer products comprise from about 0.1% to about 15% of microcapsules.

Formulations of consumer products, in which the microcapsules of the invention can be incorporated, can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

Another object of the present invention is a method for intensifying or prolonging the effect of the characteristic fragrance of a perfume ingredient on a surface, characterized in that said surface is, preferentially in the presence of light, treated with
a) a microcapsule of the invention, as defined above, containing an oil phase comprising at least one photolabile polymer generating, upon exposure to the light, a gas selected among the group consisting of CO and $CO_2$, and, optionally, comprising at least one photo-catalyst; or
b) a perfuming composition of the invention, as defined above, comprising the microcapsule of a); or
c) a perfumed consumer product, as defined above, comprising the microcapsule of a); under conditions which are susceptible of allowing the release of the oil phase.

Suitable surfaces for such treatment are in particular textiles, hard surfaces, hair and skin.

EXAMPLES

The invention is hereafter described in more detailed manner by way of the following examples, wherein the abbreviations have the usual meaning in the art, temperatures are indicated in degrees centigrade (° C.). NMR spectral data were recorded in $CDCl_3$ (if not stated otherwise) on a Bruker AMX 400 or 500 spectrometer in $CDCl_3$ at 400, 500 or 600 MHz for $^1H$ and at 100.6, 125.8 or 151.0 MHz for $^{13}C$, the chemical displacements δ are indicated in ppm with respect to $Si(CH_3)_4$ as the standard, the coupling constants J are expressed in Hz (br.=broad peak). In some cases broad peaks with low signal intensities could not unambiguously be distinguished from the baseline of their $^{13}C$ NMR spectra and were thus not assigned. Size exclusion chromatography (SEC) analyses of polymer samples were carried out at room temperature (ca. 22° C.) on a Viscotek GPC max VE 2001 GPC Solvent Sample Module connected to a Viscotek UV detector 2500, a Viscotek VE3580 RI detector and a Viscotek-270-Dual-Detector viscometer. Samples were eluted from a Waters Styragel® HR4E and HR5 column (connected in series) at a flow rate of 1.0 mL/min with tetrahydrofuran (THF, HPLC-grade). Universal calibrations were performed using commercial poly (styrene) standards. The polymer standard (ca. 40 mg) was accurately weighed and dissolved in THF (10 mL); then these solutions (100 μL) were injected for the calibration. For the molecular weights of the polymers determined by SEC, $M_w$ stands for "weight average molecular weight" and $M_n$ stands for "number average molecular weight". Average diameters of microcapsules were determined by flow particle image analysis (FPIA) on a Sysmex FPIA-3000 instrument from Malvern. Optical microscope photographs were recorded on a Leica DM RXE instrument, equipped with a DFC300FX camera using an image magnification of 1.6× and 40×. Commercially available reagents and solvents were used without further purification if not stated otherwise. Reactions were carried out in standard glassware under $N_2$.

Although specific conformations or configurations are indicated for some of the compounds, this is not meant to limit the use of these compounds to the isomers described. According to the invention, all possible conformation or configuration isomers are expected to have a similar effect.

Example 1

Preparation of a Photolabile Polymer comprising an α-Ketoester Group Capable of Generating a Gas upon Exposure to Light Preparation of poly(4-(2-hydroxyethyl)phenyl-2-oxoacetic acid) (Polymer 1)

A solution of 2-oxo-2-phenylacetic acid (9.01 g, 60.0 mmol), DMAP (0.74 g, 6.07 mmol) and 2-bromoethanol (4.15 mL, 58.8 mmol) in dichloromethane (60 mL) was cooled on an ice-bath before a solution of DCC (14.67 g, 71.1 mmol) in dichloromethane (40 mL) was added during 1 h. The reaction mixture was stirred for 3 h at 0° C., then at room temperature for 14 h. The precipitate formed in the reaction was filtered off and the filtrate taken up in ether, washed with water (2×), aqueous HCl (5%, 2×), and a saturated solution of $Na_2CO_3$ (2×). The organic layer was dried ($Na_2SO_4$) and concentrated. Column chromatography ($SiO_2$, n-heptane/ethyl acetate 4:1) gave 9.23 g (92%) of 2-bromoethyl 2-oxo-2-phenylacetate as a slightly yellow oil.

$^1H$-NMR (400 MHz): δ 8.1-8.0 (m, 2H), 7.7-7.6 (m, 1H), 7.6-7.5 (m, 2H), 4.7 (t, J=6.1, 2H), 3.6 (m, J=6.1, 2H).

$^{13}C$-NMR (100.6 MHz): δ 185.6 (s), 163.1 (s), 135.2 (d), 132.2 (s), 130.1 (s), 129.0 (d), 65.1 (t), 27.7 (t).

2-Bromoethyl 2-oxo-2-phenylacetate (6.59 g, 25.6 mmol) was suspended in dichloromethane (80 mL) at 0° C. To this mixture AlCl$_3$ (6.17 g, 46.3 mmol) was added in small portions during 30 min while keeping the temperature below to 15° C. The mixture was stirred at room temperature for 20 h. Then toluene (1.8 mL, 29.2 mmol) was added and the reaction mixture stirred at room temperature for 2 h. The mixture was poured onto crushed ice (300 g) and concentrated hydrochloric acid (100 mL, extracted with dichloromethane (80 mL), the organic layer washed with aqueous sodium hydroxide (0.1 N, 100 mL) and a saturated aqueous solution of NaCl (100 mL), dried (MgSO$_4$) and concentrated. Column chromatography (SiO$_2$, ethyl acetate/n-heptane 4:1) gave 1.27 g of a yellow oil. M. (SEC)=4800 Da, M, (SEC)=6000 Da.

$^1$H-NMR (500 MHz): δ 8.3-6.8 (m, 4H), 2.8 (m, 2H), 2.3 (m, 2H).

Preparation of poly(methyl 2-oxo-2-(4-vinylphenyl) acetate)-co-poly(styrene) (Polymer 2)

A solution of methyl 2-chloro-2-oxoacetate (11.03 g, 90 mmol, origin: Alfa Aesar) in dichloromethane (50 mL) was added dropwise during 30 min to a suspension of AlCl$_3$ (12.00 g, 90 mmol) in dichloromethane (200 mL), which was cooled to 3-5° C. with an ice-bath. The reaction mixture was stirred at 3-5° C. for 30 min. Then a solution of styrene (7.81 g, 75 mmol) dissolved in dichloromethane (100 mL) was added dropwise at 3-5° C. during 35 min and the reaction mixture stirred at 3-5° C. for 105 min. The reaction mixture was poured onto ice (100 g) and the reaction flask rinsed with water (100 mL) and dichloromethane (100 mL). The mixture was decanted and the aqueous layer extracted with dichloromethane (2×, 100 mL). The organic layers were washed with water (100 mL), with an aqueous solution of NaHCO$_3$ (10%, 100 mL) and again with water (100 mL). Drying (Na$_2$SO$_4$) and evaporating the solvent under reduced pressure (at 45° C.) gave 17.35 g of the random co-polymer as a slightly yellow powder, still containing some ethyl acetate. Monomer distribution ($^1$H-NMR): ca. 1:2. M$_n$ (SEC)=4400 Da, M, (SEC)=28250 Da.

$^1$H-NMR (400 MHz, DMSO-D$_6$): δ 8.0-6.1 (br. m, 14H), 3.9 (br. s, 3H), 2.4-0.6 (br. m, 7H).

$^{13}$C-NMR (100.6 MHz, DMSO-D$_6$): δ 186.0 (br. s), 164.2 (br. s), 153.3 (br. s), 144.3 (br. s), 129.6 (br. d), 128.0 (br. d), 127.1 (br. d), 125.7 (br. d), 52.8 (q), 41.5 (br. t), 39.9 (br. d).

Preparation of poly(ethyl 2-oxo-2-(4-vinylphenybacetate)-co-poly(styrene) (Polymer 3)

A solution of ethyl 2-chloro-2-oxoacetate (25.08 g, 180 mmol, origin: Alfa Aesar) in dichloromethane (100 mL) was added dropwise during 55 min to a suspension of AlCl$_3$ (24.24 g, 180 mmol) in dichloromethane (400 mL), which was cooled to 3-5° C. with an ice-bath. The reaction mixture was stirred at 3-5° C. for 2.5 h. Then a solution of styrene (15.62 g, 150 mmol) dissolved in dichloromethane (100 mL) was added dropwise at 3-5° C. during 35 min and the reaction mixture stirred at 3-5° C. for 1.5 h. After warming to room temperature overnight the reaction mixture was poured onto ice (200 g) and the reaction flask rinsed with dichloromethane (200 mL) and some water to form a white emulsion. Dilution with ethyl acetate, decanting, washing the organic phase with an aqueous solution of NaHCO$_3$ (10%), a saturated aqueous solution of NaCl, drying (Na$_2$SO$_4$) and evaporating the solvent under reduced pressure (at 45° C.) gave 22.03 g of the random co-polymer as a slightly yellow powder, still containing some ethyl acetate. Monomer distribution ($^1$H-NMR): ca. 1:1.4 M$_n$ (SEC)=6900 Da, M, (SEC)=51400 Da.

$^1$H-NMR (500 MHz, DMSO-D$_6$): δ 8.0-6.0 (br. m, 11.0H), 4.6-4.3 (br. m, 2H), 2.5-1.2 (m, 10.2H).

$^{13}$C-NMR (125.8 MHz, DMSO-D$_6$): δ 186.3 (br. s), 164.0 (br. s), 153.6 (br. s), 144.2 (br. s), 129.7 (br. d), 128.1 (br. d), 127.2 (br. d), 125.7 (br. d), 62.2 (t), 42.8 (br. t), 40.0 (br. d), 13.8 (q).

Alternative Preparation of poly(ethyl 2-oxo-2-(4-vinylphenybacetate)-co-poly(styrene) (Polymer 4)

Copper(I)bromide (35.8 mg, 0.250 mmol) was added under nitrogen to a mixture of styrene (5.5 mL, 48.0 mmol) and N-(2-(dimethylamino)ethyl)-N,N',N''-trimethylethane-1,2-diamine (1.05 mL, 5.0 mmol). Oxygen was removed from the solution in three freeze-pump-thaw cycles. Then 2-bromopropanenitrile (0.43 mL, 4.97 mmol) was added under nitrogen. The reaction mixture was stirred at 110° C. for 4 h before slowly being cooled to room temperature. Then ethyl acetate (50 mL) was added and the reaction mixture filtered through a sintered glass funnel. The organic layer was washed with water (3×50 mL), dried (MgSO$_4$), filtered and concentrated to give 3.30 g of polystyrene as a white solid. M$_n$ (SEC)=1200 Da, M$_w$, (SEC)=1450 Da.

A suspension of AlCl$_3$ (5.11 g, 37.9 mmol) in dichloromethane (100 mL) was cooled with an ice bath to 3-5° C., before a solution of ethyl 2-chloro-2-oxoacetate (5.28 g, 37.9 mmol) in dichloromethane (25 mL) was added dropwise during 15 min. The reaction mixture was stirred at 3-5° C. for 45 min. Then polystyrene (M$_n$=1200 Da, prepared as described above, 3.29 g, 31.6 mmol) in dichloromethane (25 mL) was added during 30 min. The mixture was diluted with dichloromethane (25 mL) and left stirring at 3-5° C. for 3 h. An aliquot of the reaction mixture (50 mL) was poured onto ice and extracted with ethyl acetate (200 mL), washed with a saturated solution of NaCl (2×50 mL), an aqueous solution of NaHCO$_3$ (10%, 50 mL), and again with a saturated solution of NaCl (50 mL). Re-extraction of the aqueous phases with ethyl acetate (100 mL), drying of the combined organic phases (Na$_2$SO$_4$), concentrating (10 mbar, 45° C.) and drying under vacuum (0.2 mbar, room temperature) gave 1.16 g of the random co-polymer as a white powder, still containing some ethyl acetate. Monomer distribution ($^1$H-NMR): ca. 1:1.4, which corresponds to an amount of grafting of ca. 42%.

$^1$H-NMR (500 MHz, DMSO-D$_6$): δ 8.0-6.2 (br. m, 9H), 4.6-4.3 (br. m, 2H), 2.6-0.9 (m, 9H).

$^{13}$C-NMR (125.8 MHz, DMSO-D$_6$): δ 186.3 (br. s), 164.0 (br. s), 153.6 (br. s), 143.9 (br. s), 129.7 (br. d), 128.1 (br. d), 127.3 (br. d), 125.8 (br. d), 62.2 (t), 13.8 (q).

Further Preparation of poly(ethyl 2-oxo-2-(4-vinylphenyl) acetate)-co-poly(styrene) (Polymer 5)

Copper(I)bromide (64.4 mg, 0.449 mmol) in toluene (5 mL) was added under nitrogen to a mixture of styrene (11 mL, 96.0 mmol) and N-(2-(dimethylamino)ethyl)-N,N',N''-trimethylethane-1,2-diamine (2.1 mL, 10.1 mmol). Oxygen was removed from the solution in freeze-pump-thaw cycles. Then 2-bromopropanenitrile (0.86 mL, 10.0 mmol) was added under nitrogen. The reaction mixture was stirred at 110° C. for 14 h before slowly being cooled to room temperature. The reaction mixture was diluted with ethyl acetate (50 mL) and washed with water (3×50 mL), dried (MgSO$_4$), filtered and concentrated to give 5.80 g of polystyrene as a white solid. M$_n$ (SEC)=1450 Da, M, (SEC)= 2050 Da.

A suspension of AlCl$_3$ (9.00 g, 66.8 mmol) in dichloromethane (200 mL) was cooled with an ice bath to 3-5° C., before a solution of ethyl 2-chloro-2-oxoacetate (9.31 g, 66.8 mmol) in dichloromethane (50 mL) was added dropwise during 30 min. More dichloromethane (10 mL) was added and the reaction mixture stirred at 3-5° C. for 30 min. Then polystyrene (5.80 g, 55.7 mmol) in dichloromethane (50 mL) was added during 30 min. The mixture was diluted with dichloromethane (10 mL) and left stirring at 3-5° C. for 1.5 h. The reaction mixture was poured onto ice (100 g) and extracted with ethyl acetate (500 mL), washed with a saturated solution of NaCl (100 mL), a saturated aqueous solution of NaHCO$_3$ and NaCl (1:1, 200 mL), and again with a saturated solution of NaCl (100 mL). Re-extraction of the aqueous phases with ethyl acetate (150 mL), drying of the combined organic phases (Na$_2$SO$_4$), concentrating (4 mbar, 45° C.) and drying under vacuum (0.8 mbar, room temperature) gave 11.24 g of the random co-polymer as a slightly yellow powder. Monomer distribution ($^1$H-NMR): ca. 1:1.9, which corresponds to an amount of grafting of ca. 34%. Similar NMR spectra as those reported above (Polymer 4) were obtained.

Preparation of poly(vinyl 2-oxo-2-phenylacetate)-co-poly(vinyl alcohol) (Polymer 6)

Poly(vinyl alcohol) (PVOH 98-4, M, ~27 000 Da, 0.56 g, 12.7 mmol, origin: Fluka) in DMSO (25 mL) was heated to 70° C., then K$_2$CO$_3$ (0.34 g, 2.5 mmol) and methyl 2-oxo-2-phenylacetate (2.00 g, 12.2 mmol, origin: PCAS) were added and the mixture stirred at 70-80° C. overnight. After cooling to room temperature, the solvent was removed by bulb-to-bulb distillation (80° C. to 180° C., 0.08 mbar). The residue was washed with a mixture of water (10 mL) and ethyl acetate (15 mL), then with a mixture of water (10 mL) and dichloromethane (15 mL), decanted and dried under vacuum (0.08 mbar, room temperature). The polymer was dissolved in DMSO (5 mL) at 35° C. and precipitated by adding the solution dropwise into cold diethyl ether. Filtration through a sintered glass frit, washing with cold diethyl ether and drying under vacuum (0.08 mbar, room temperature) until reaching a constant mass afforded 0.7 g of the random co-polymer as a highly viscous yellow oil, still containing some ethyl acetate. Amount of grafting ($^1$H-NMR): ca. 18%.

$^1$H-NMR (400 MHz, DMSO-D$_6$): δ 8.1-7.9 (br. m, 2H), 7.9-7.7 (br. m, 1H), 7.7-7.5 (br. m, 2H), 5.7-5.4 (br. m, 1H), 4.9-4.2 (br. m, 4.5H), 4.1-3.6 (br. m, 4.5H), 2.1-1.2 (br. m, 11H).

$^{13}$C-NMR (100.6 MHz, DMSO-D$_6$): δ 187.2 (br. s), 163.5 (br. s), 135.3 (d), 131.6 (s), 129.6 (d), 129.2 (d), 72.6 (br. d), 67.7 (br. d), 65.5 (br. d), 63.7 (br. d), 46.1 (br. t), 45.7 (br. t), 45.2 (br. t), 44.6 (br. t), 42.7 (br. t), 42.0 (br. t), 41.8 (br. t).

Preparation of poly(2-(2-oxo-2-phenylacetoxy)ethyl methacrylate)-co-poly(2-hydroxyethyl methacrylate)-co-poly(butyl methacrylate) (Polymer 7)

Copper(I)bromide (33.9 mg, 0.236 mmol) was added under nitrogen to a mixture of 2-hydroxyethyl methacrylate (4.5 mL, 37.1 mmol), butyl methacrylate (5.9 mL, 37.1 mmol) and N-(2-(dimethylamino)ethyl)-N,N',N''-trimethylethane-1,2-diamine (2.1 mL, 10.06 mmol). Oxygen was removed from the solution in freeze-pump-thaw cycles. Then 2-bromopropanenitrile (0.87 mL, 10.07 mmol) was added under nitrogen. The reaction mixture was stirred at 90° C. for 4 h before slowly being cooled to room temperature. Then ethyl acetate (50 mL) was added and the reaction mixture filtered through a sintered glass funnel. The organic layer was washed with water (3×50 mL), dried (MgSO$_4$), filtered and concentrated to give 9.0 g of poly(2-hydroxyethyl methacrylate)-co-poly(butyl methacrylate) as a random co-polymer. Monomer distribution ($^1$H-NMR): ca. 1:1.2. M$_n$ (SEC)=1050 Da, M, (SEC)=2150 Da.

$^1$H-NMR (500 MHz): δ 4.4-4.0 (br. m, 2H), 4.0-3.9 (br. m, 2H), 3.9-3.8 (br. m, 2H), 2.2-0.8 (br. m, 18H).

$^{13}$C-NMR (125.8 MHz): δ 177.9 (s), 177.2 (br. s), 66.9 (br. t), 65.1 (br. t), 60.4 (br. t), 54.3 (br. t), 44.8 (br. s), 30.2 (t), 19.3 (t), 20.0 (br. q), 17.1 (br. q), 13.7 (q).

A solution of 2-oxo-2-phenylacetic acid (7.04 g, 45.9 mmol), N,N-dimethylpyridin-4-amine (DMAP, 3.02 g, 24.5 mmol) and poly(2-hydroxyethyl methacrylate)-co-poly(butyl methacrylate) (7.91 g, 30.6 mmol) in dichloromethane (100 mL) was cooled with an ice bath to 3-4° C., before a solution of N,N'-methanediylidenedicyclohexanamine (7.02 g, 33.7 mmol) in dichloromethane (75 mL) was added dropwise under stirring during 45 min. More dichloromethane (10 mL) was added and the reaction mixture left warming to room temperature overnight. The suspension was filtered, rinsed with dichloromethane (100 mL) and the filtrate washed with HCl (10%, 50 mL), demineralized water (100 mL), an aqueous solution of NaHCO$_3$ (10%, 100 mL) and water (100 mL). The aqueous phases were re-extracted with dichloromethane. Drying of the combined organic phases (Na$_2$SO$_4$), concentrating (10 mbar, 45° C.) and drying under vacuum gave 10.98 g of the random co-polymer. Monomer distribution ($^1$H-NMR): ca. 0.85:0.15: 1.2, which corresponds to an amount of grafting of ca. 85% (with respect to the total amount of available hydroxyl groups).

$^1$H-NMR (400 MHz): δ 8.1-7.9 (br. m, 2H), 7.7-7.6 (br. m, 1H), 7.6-7.4 (br. m, 2H), 4.7-4.5 (br. m, 2H), 4.5-4.2 (br. m, 2H), 4.1-3.8 (br. m, 2H), 2.2-0.7 (br. m, 17H).

$^{13}$C-NMR (100.6 MHz): δ 185.4 (s), 177.3 (br. s), 176.2 (br. s), 163.3 (s), 135.0 (d), 132.3 (s), 130.1 (d), 129.0 (d), 64.8 (br. t), 63.1 (br. t), 62.1 (br. t), 54.3 (br. t), 44.7 (br. s), 30.2 (br. t), 19.3 (t), 18.3 (br. q), 16.7 (br. q), 13.7 (q).

Preparation of poly(ethyl 2-oxo-2-(4-vinylphenybacetate)-co-poly(styrene)-co-poly(methyl methacrylate) (Polymer 8)

Copper(I)bromide (41.3 mg, 0.288 mmol) was added under nitrogen to a mixture of styrene (5.5 mL, 47.8 mmol), methyl methacrylate (5.1 mL, 47.7 mmol) and N-(2-(dimethylamino)ethyl)-N,N',N''-trimethylethane-1,2-diamine (2.1 mL, 10.06 mmol). Oxygen was removed from the solution in freeze-pump-thaw cycles. Then 2-bromopropanenitrile (0.87 mL, 10.07 mmol) was added under nitrogen. The reaction mixture was stirred at 110° C. for 3 h before slowly being cooled to room temperature. Then ethyl acetate (50 mL) was added and the reaction mixture filtered through a sintered glass funnel. The organic layer was washed with water (3×50 mL), dried (MgSO$_4$), filtered, concentrated and dried under vacuum to give 8.6 g of poly(styrene)-co-poly(methyl methacrylate) as a random co-polymer. Monomer distribution ($^1$H-NMR): ca. 1:1.1. M$_n$ (SEC)=1450 Da, M, (SEC)=1900 Da.

$^1$H-NMR (400 MHz): δ 7.5-6.4 (br. m, 5H), 3.8-2.7 (br. m, 3H), 2.7-1.4 (br. m, 5H), 1.4-0.3 (br. m, 3H).

$^{13}$C-NMR (100.6 MHz): δ 176.7 (br. s), 145.0 (br. s), 128.2 (br. d), 127.6 (br. d), 127.5 (br. d), 126.1 (br. d), 51.6 (br. q), 50.9 (br. q), 45.5 (br. s), 44.3 (br. s), 42.7 (br. t), 38.4 (br. d), 22.7 (br. q), 21.4 (br. q).

A suspension of AlCl$_3$ (58.50 g, 434.0 mmol) in dichloromethane (500 mL) was cooled with an ice bath to 3-5° C., before a solution of ethyl 2-chloro-2-oxoacetate (17.68 g, 127.0 mmol) in dichloromethane (100 mL) was added dropwise during 30 min. The mixture was diluted with dichloromethane (20 mL) and left stirring at 3-5° C. for 30 min. More dichloromethane (250 mL) was added and the mixture stirred for 15 min. Then poly(styrene)-co-poly (methyl methacrylate) ($M_n$=1450 Da, prepared as described above, 8.56 g, 41.9 mmol) in dichloromethane (150 mL) was added during 30 min. The mixture was diluted with dichloromethane (100 mL) and left warming to room temperature overnight. The reaction mixture was poured onto crushed ice (500 g) and extracted with ethyl acetate (2×250 mL), washed with an aqueous solution of NaCl (20%, 3×250 mL), a saturated solution of NaCl (250 mL). The combined organic phases were dried ($Na_2SO_4$), concentrated and dried under vacuum (0.2 mbar, room temperature) to give 11.07 g of the random co-polymer as a beige powder. Monomer distribution ($^1$H-NMR): ca. 0.4:0.6:1.1, which corresponds to an amount of grafting of ca. 40%. $M_n$ (SEC)=2050 Da, M, (SEC)=3250 Da.

$^1$H-NMR (500 MHz, DMSO-$D_6$): δ 8.2-6.7 (br. m, 4.6H), 4.6-4.3 (br. m, 0.8H), 3.7-2.7 (br. m, 3.3H), 2.1-1.4 (br. m, 5.2H), 1.4-1.2 (br. m, 1.2H), 1.2-0.2 (br. m, 3.3H).

$^{13}$C-NMR (125.8 MHz, DMSO-$D_6$): δ 188.2 (s), 186.3 (s), 176.5 (br. s), 175.8 (br. s), 166.2 (s), 163.8 (s), 153.2 (br. s), 143.5 (br. s), 129.9 (br. d), 128.6 (br. d), 128.1 (br. d), 127.8 (br. d), 125.8 (br. d), 122.6 (br. s), 62.2 (t), 51.3 (br. q), 50.6 (br. q), 49.7 (br. t), 45.0 (br. s), 43.8 (br. s), 38.2 (br. d), 20.0 (br. q), 17.8 (br. q), 13.8 (q).

Example 2

Preparation of Microcapsules According to the Present Invention Containing a Photolabile Polymer Capable of Generating a Gas upon Exposure to Light and a Fragrance Molecule as the Oil Phase Preparation of Microcapsules According to the Present Invention Containing a Photolabile Polymer 5

A mixture of Takenate® D110 N (1.78 g, 4.7 mmol, origin: Mitsui Chemicals), acetophenone (fragrance, 6.54 g, 54.4 mmol) and poly(ethyl 2-oxo-2-(4-vinylphenyl)acetate)-co-poly(styrene) (Polymer 5 prepared in Example 1, 6.53 g, 19.3 mmol) was stirred for 2 min. Poly(vinyl alcohol) (PVOH 18-88, 1% in water, 42.14 g, 3.2 μmol, origin: Aldrich) was added and an emulsion was obtained by Ultra-Turrax stirring (model S25N 10G/4) at 17,500 rpm during 2 min (23° C./pH 4.6). The droplet size was controlled by light microscopy and the pH was adjusted with sodium hydroxide at 5.07. The mixture was transferred to a 250 mL reactor and stirred at 350 rpm at room temperature. A solution of 1H-1,2,4-triazole-3,5-diamine (0.32 g, 3.2 mmol, origin: Alfa Aesar) in water (5.01 g, 278.0 mmol) was added dropwise during 1 h. The reaction mixture was stirred at 350 rpm at 70° C. for 1 h. At the end of process, the capsule slurry (pH 4.68) was cooled to room temperature. Capsules with an average size of 9.7 μm were obtained.

Preparation of Microcapsules According to the Present Invention Containing a Photolabile Polymer 7

A mixture of Takenate® D110 N (2.38 g, 6.2 mmol), methyl 2,2-dimethyl-6-methylenecyclohexanecarboxylate (Romascone®, fragrance, 5.78 g, 31.7 mmol, origin: Firmenich SA), benzyl benzoate (fragrance, 5.78 g, 27.2 mmol) and poly(2-(2-oxo-2-phenylacetoxy)ethyl methacrylate)-co-poly(butyl methacrylate) (Polymer 7 prepared in Example 1, 5.78 g, 14.3 mmol) was stirred for 2 min. PVOH 18-88 (1% in water, 42.01 g, 3.2 μmol) was added and an emulsion was obtained by Ultra-Turrax stirring (model S25N 10G/4) at 17,500 rpm during 2 min (23° C./pH 4.6). The droplet size was controlled by light microscopy and the pH was adjusted with sodium hydroxide at 5.09. The mixture was transferred to a 250 mL reactor and stirred at 350 rpm at 25° C. A solution of 1H-1,2,4-triazole-3,5-diamine (0.43 g, 4.4 mmol) in water (5.02 g, 279.0 mmol) was added dropwise during 1 h. The reaction mixture was stirred at 350 rpm at 70° C. for 2 h. At the end of process, the capsule slurry (pH 5.36) was cooled to room temperature. Capsules with an average size of 18.8 μm were obtained.

Preparation of Microcapsules According to the Present Invention Containing a Photolabile Polymer 8

A mixture of Takenate® D110 N (0.96 g, 2.5 mmol), ethyl 2-oxo-2-phenylacetate (1.77 g, 10.0 mmol, origin: Alfa Aesar), acetophenone (fragrance, 1.90 g, 15.9 mmol), 2-phenylethyl 2-oxo-2-phenylacetate (profragrance, 1.75 g, 6.9 mmol) and poly(ethyl 2-oxo-2-(4-vinylphenyl)acetate)-co-poly(styrene)-co-poly(methyl methacrylate) (Polymer 8 prepared in Example 1, 1.75 g, 5.2 mmol) was stirred for 2 min. PVOH 18-88 (1% in water, 56.34 g, 4.3 μmol) was added and an emulsion was obtained by Ultra-Turrax stirring (model S25N 10G/4) at 17,500 rpm during 2 min (23° C./pH 4.6). The droplet size was controlled by light microscopy and the pH was adjusted with sodium hydroxide at 5.09. The mixture was transferred to a 250 mL reactor and stirred at 350 rpm at 25° C. A solution of 1H-1,2,4-triazole-3,5-diamine (0.18 g, 1.8 mmol) in water (5.02 g, 279.0 mmol) was added dropwise during 1 h. The reaction mixture was stirred at 350 rpm at 70° C. for 2 h. At the end of process, the capsule slurry (pH 5.27) was cooled to room temperature. Capsules with an average size of 12.7 μm were obtained.

Example 3

Observation of the Formation of a Gas upon Exposure of a Photolabile Polymer Comprising an α-Ketoester to UVA Light To verify the generation of a gas upon exposure to UVA light the photolabile polymers comprising an sa-ketoester according to the invention were dissolved in different fragrance raw materials (50% by weight; poly(ethyl 2-oxo-2-(4-vinylphenyl)acetate)-co-poly(styrene) (Polymer 4) in acetophenone, poly(2-(2-oxo-2-phenylacetoxy)ethyl methacrylate)-co-poly(2-hydroxyethyl methacrylate)-co-poly (butyl methacrylate) (Polymer 7) in benzyl benzoate, poly (ethyl 2-oxo-2-(4-vinylphenyl)acetate)-co-poly(styrene)-co-poly(methyl methacrylate) (Polymer 8) in acetophenone). A few drops of these solutions were then placed on a microscope glass slide, carefully covered with a second glass slide and analyzed by optical microscopy. White light was used to localize the bubbles on the glass slide and a first image was taken before irradiation (0 s). Then the UVA light (340-380 nm) of the microscope was switched on and a second image was taken after 25 s of irradiation. As illustrated in FIG. 1, the formation of the gas as a consequence of the exposure to UVA light was clearly observed, thus indicating the cleavage of the 2-oxoacetate.

What is claimed is:

1. A non-diffusive microcapsule comprising:
A) a core comprising, or consisting of:
   an oil phase;
   at least one photolabile linear or graft polymer comprising an α-ketoacid or α-ketoester group capable of generating, upon exposure to light a gas selected among the group consisting of CO and $CO_2$ and comprising at least one unit of formula

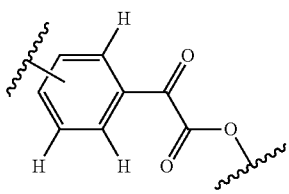
(I)

wherein said unit of formula (I) comprises a benzenediyl functional group substituted in meta or para and is part of:
a) a backbone of a linear polymer of formula

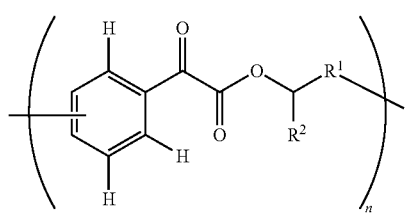
(II)

wherein n represents an integer varying between 2 and 1000, $R^1$ represents a $C_{1-8}$ hydrocarbon group and $R^2$ represents a hydrogen atom or a methyl group; or
b) a side chain of a graft polymer of formula

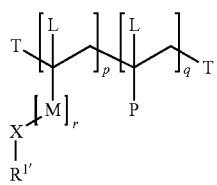
(III)

wherein
M represents a $C_{1-8}$ aliphatic hydrocarbon group optionally comprising one or two oxygen atoms and/or one nitrogen atom;
P represents a $OR^3$; a $COOR^3$ group, a $COOCH_2C_6H_5$ group, a $COOC_6H_5$ group, a $C_6H_5$ group, a $C_6H_4COOR^3$ group, a $C_6H_4OH$ group, a $OC(=O)R^3$ group, a $CON(R^3)_2$, a 2-oxopyrrolidin-1-yl or a 2-oxoazepan-1-yl wherein $R^3$ represents a hydrogen atom, a $C_{1-18}$ alkyl group, a $(CH_2CH_2)_{1-3}OH$ group;
L is a hydrogen atom or a methyl group;
X represents the unit of formula (I) provided that the oxygen atom of the carboxyl functional group of the unit (I) is linked to a primary or secondary carbon atom;

$R^1$ represents a hydrogen atom, a $C_{1-22}$ hydrocarbon group optionally comprising one to three oxygen atoms and/or one to two nitrogen atoms and/or one sulfur atom, or, if $R^1$ is linked to the oxygen atom of the carboxyl functional group of the unit (I), an alkaline metal ion;
p is an integer varying between 5 and 1000;
q is an integer varying between 0 and 500;
r is an integer varying between 0 and 1; and
T is a polymer terminating group;
optionally comprising at least one photo-catalyst; and
B) a shell surrounding said core formed by interfacial polymerization, by a phase separation process induced by polymerization or by coacervation.

2. A microcapsule according to claim 1, characterized in that said microcapsules comprise, based on the total microcapsule weight, from about 20% to about 96% by weight of oil phase.

3. A microcapsule according to claim 1, wherein $R^1$ represents a $C_{1-8}$ aliphatic hydrocarbon.

4. A microcapsule according to claim 1, wherein the photolabile polymer is a polymer of formula (III).

5. A microcapsule according to claim 4, wherein M represents a group of formula

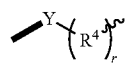
a)

wherein the wavy line indicates the location of the bond between M and X, and the bold line indicates the location of the bond between M and the unit of formula $[C(L)CH_2]_P$, and wherein Y represents an oxygen atom, or a carboxyl functional group, $R^4$ represents $C_{1-7}$ aliphatic hydrocarbon group and r is an integer varying between 0 and 1 providing that r is equal to 0 only when Y is a carboxyl functional group.

6. A microcapsule according to claim 4, wherein $R^1$ represents a $C_{2-10}$ alkyl group optionally comprising one to three oxygen atoms and/or one or two nitrogen atoms.

7. A microcapsule according to claim 6, wherein the α-ketoacid or α-ketoester group generates a gas upon exposure to light at a wavelength comprised between 450 and 320 nm.

8. A microcapsule according to claim 7, wherein said microcapsules comprise, based on the total microcapsule weight, from about 10% to about 50% by weight of photolabile polymer.

9. A microcapsule according to claim 1, wherein said shell surrounding said core is an aminoplast, polyamide, polyester, polyurea or polyurethane resins or a mixture thereof.

10. A microcapsule according to claim 1, wherein said shell has a thickness varying between 20 and 500 nm.

11. A microcapsule according to claim 1, wherein the oil phase contains a perfuming oil.

12. A perfuming consumer product comprising:
i) as a perfuming ingredient, at least one microcapsule, defined in claim 11; and
ii) optionally a free perfume oil.

13. A perfuming consumer product according to claim 12, wherein the perfumery consumer product is a perfume, a fabric care product, a body-care product, an air care product or a home care product.

14. A perfuming consumer product according to claim 12, wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

15. A method for intensifying or prolonging fragrance of a perfume ingredient on a surface, which comprises treating the surface with a microcapsule as defined in claim 11 in the presence of light under conditions which are susceptible of allowing release of the perfume oil.

16. A method for intensifying or prolonging fragrance of a perfume ingredient on a surface, which comprises treating the surface with a perfuming consumer product as defined in claim 12 in the presence of light under conditions which are susceptible of allowing release of the perfume oil.

17. The method of claim 16 wherein the perfumery consumer product is a perfume, a fabric care product, a body-care product, an air care product or a home care product.

18. The method of claim 16 wherein the perfumery consumer product is a fine perfume, a cologne, an after-shave lotion, a liquid or solid detergent, a fabric softener, a fabric refresher, an ironing water, a paper, a bleach, a shampoo, a coloring preparation, a hair spray, a vanishing cream, a deodorant or antiperspirant, a perfumed soap, shower or bath mousse, oil or gel, a hygiene product, an air freshener, a "ready to use" powdered air freshener, a wipe, a dish detergent or hard-surface detergent.

* * * * *